(12) United States Patent  
Burnside et al.

(10) Patent No.: US 6,979,329 B2  
(45) Date of Patent: Dec. 27, 2005

(54) MEDICAL PROBE WITH REDUCED NUMBER OF TEMPERATURE SENSOR WIRES

(75) Inventors: Robert R. Burnside, Mountain View, CA (US); Russell B. Thompson, Los Altos, CA (US); David Dueiri, San Jose, CA (US); Dennis M. O'Brien, Carlsbad, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 196 days.

(21) Appl. No.: 10/307,709

(22) Filed: Dec. 3, 2002

(65) Prior Publication Data

US 2003/0120271 A1    Jun. 26, 2003

Related U.S. Application Data

(63) Continuation of application No. 09/609,604, filed on Jun. 30, 2000, now Pat. No. 6,511,478.

(51) Int. Cl.[7] .............................................. A61B 18/18
(52) U.S. Cl. ....................................................... 606/41
(58) Field of Search ................................... 606/27–52

(56) References Cited

U.S. PATENT DOCUMENTS

| 4,459,042 A |   | 7/1984  | Paros et al. |
|---|---|---|---|
| 5,359,993 A | * | 11/1994 | Slater et al. ................ 600/133 |
| 5,456,682 A |   | 10/1995 | Edwards et al. |
| 5,688,266 A |   | 11/1997 | Edwards et al. |
| 5,688,267 A |   | 11/1997 | Panescu et al. |
| 5,769,847 A |   | 6/1998  | Panescu et al. |
| 5,782,828 A |   | 7/1998  | Chen et al. |
| 5,810,802 A | * | 9/1998  | Panescu et al. ................ 606/31 |
| 5,837,001 A |   | 11/1998 | Mackey |
| 5,928,228 A |   | 7/1999  | Kordis et al. |
| 6,162,184 A |   | 12/2000 | Swanson et al. |
| 6,197,021 B1 |  | 3/2001  | Panescu et al. |

FOREIGN PATENT DOCUMENTS

| EP | 0 991 364 | 12/2000 |
|---|---|---|
| WO | WO 96/00036 | 4/1996 |

* cited by examiner

*Primary Examiner*—Michael Peffley  
*Assistant Examiner*—Pete Vrettakos  
(74) *Attorney, Agent, or Firm*—Bingham McCutchen LLP

(57) ABSTRACT

Systems and methods for reducing the number of temperature measurement wires in multiple temperature sensor ablation systems are described. In a preferred embodiment, temperature sensors capable of measuring the temperature of body tissue and transmitting the temperature data digitally are incorporated in a catheter or probe ablation system that also includes electrodes in operative contact with the sensors. The sensors are connected in parallel to a common electrical bus, thereby allowing the system to operate using a reduced number of electrical paths as compared to conventional ablation systems. The present invention is also directed to ablation systems that incorporate analog sensors rather than digital sensors. In this embodiment, the system utilizes digital switching, filtering circuits, or oscillators to reduce the number of wires required to operate the sensors.

19 Claims, 17 Drawing Sheets

MEDICAL PROBE WITH REDUCED NUMBER OF TEMPERATURE SENSOR WIRES

CONTINUING DATA

This application is a continuation of Ser. No. 09/609,604 Jun. 30, 2000 now U.S Pat. No. 6,511,478.

FIELD OF THE INVENTION

The present inventions relate to medical probes, and more particularly, catheters and surgical probes that possess temperature sensing functionality.

BACKGROUND

Currently, medical probes, such as catheters and surgical probes, are used to treat heart abnormalities, such as atrial fibrillation and other cardiac arrythmias. In a typical procedure, a medical probe employs one or more ablation elements and one or more corresponding temperature sensors in order to therapeutically ablate tissue within the heart in a controlled manner. Temperature sensors currently used in medical probes, such as thermistors or thermocouples, all require separate analog signal conditioning circuitry for each sensor, although analog to digital (A/D) conversion circuitry may be multiplexed.

Thermistors respond to changes in temperature with a well-defined change in resistance. Analog conditioning circuitry, which is used to interface the thermistors with the A/D converter, measures the resistance of the thermistors, and thus, the temperature of the adjacent tissue, by separately measuring the voltage across each thermistor in response to a constant current. By comparison, thermocouples contain a junction of dissimilar metals that generate a small voltage proportional to temperature, due to the Peltier effect. Analog conditioning circuitry is connected to each thermocouple to amplify the voltage output thereby and to reduce any noise associated with such voltage.

Further, to support such multiple sensor probes, current technology requires a large number of wires to be contained within the small and limited space of the probe body, thereby rendering manufacture of such medical probes increasingly difficult. This constraint is even more pronounced in catheters, the diameters of which must be minimized to allow the catheters to be introduced into the heart through the vasculature of a patient. The increased number of wires in connectors and cabling also makes the manufacture of accessory cables used to support multiple sensor medical probes more difficult and expensive. Moreover, connector reliability is reduced due to the large number of connections required to implement discrete wires for each temperature sensor.

Regardless of the type of sensor utilized, the analog conditioning circuitry must be duplicated with the currently available designs for each sensor. For example, FIG. 29 illustrates a prior art system, which includes a power generator 66 that is coupled to a medical probe 50 via a cable 55. A standard generator interface 62 is used to interface the proximal end of the cable 55 to the circuitry within the generator 66, and a standard probe interface 62 is used to interface the distal end of the cable 55 to the circuitry within the medical probe 50. The power generator 66 includes a power source 51 (in this case an RF oscillator), which provides RF power to ablation energy electrodes 53 located at the distal end of the medical probe 50. The power generator 66 further includes a temperature controller 54 (in this case, a microprocessor), which communicates with analog temperature sensors 52 located at the distal end of the medical probe 50 via parallel sets of analog to digital converters 56 and signal conditioners 60. As illustrated, a separate analog to digital converter 56 and signal conditioners 60 is required for each temperature sensor 52.

FIG. 30 illustrates another prior art system, which includes a power generator 68 that is coupled to the medical probe 50 via the cable 55. The power generator 68 differs from the power generator 66 shown in FIG. 29 in that the power generator 68 uses a single analog to digital converter with multiplexing capability 58 to process signals from each sensor 52.

The additional circuitry required for each sensor 52 generally involves expensive, low noise integrated circuits. Time consuming calibration of each input during manufacturing is also typically required. As a result, the amount of circuit duplication increases by the number of sensors that must be read, thereby making systems with more than a few temperature sensors expensive and impractical. Also, the ablation power generators that support these medical probes are necessarily designed in a non-optimal manner. For a multiple sensor medical probe, the ablation power generators must be designed to accommodate the number of expected sensors by providing separate analog inputs for each sensor, as illustrated in FIGS. 29 and 30. Therefore, when designing such power generators, a tradeoff must be made between the excessive costs of providing extra sensor inputs to accommodate future requirements and the risk of premature obsolescence of a power generator that provides too few sensor inputs.

Moreover, the sensors are typically located from between ten to fifty feet away from the ablation power generators, being connected through fine-gauge wire in the medical probe itself, and through one or more cables with intermediate connections. The analog voltages which represent the temperature are typically quite small, particularly with thermocouples, where the dynamic range in the area of interest is usually only in the hundreds of microvolts. These analog voltages are susceptible to electrical noise induced by ablation power and sources of electromagnetic interference in the environment, some of which may be of a high enough amplitude or low enough frequency range that filtering may not be practical.

Consequently, there is a need to provide a medical probe system that contains a reduced number of electrical paths, or temperature sensor wires, as well as a medical probe system that outputs temperature sensor signals that exhibit little or no noise.

SUMMARY OF THE INVENTION

The present inventions are directed to medical probe systems, medical probes, ablation power generators, and temperature sensor subassemblies that are configured to reduce the number of wires used to conduct data output from a multitude of temperature sensors. The present inventions are also directed to medical probes that utilize one or more digital temperature sensors, resulting in a temperature sensing circuit that is less susceptible to ambient noise.

In accordance with a first aspect of the present inventions, a medical probe comprises an elongate member having a proximal end and a distal end. The medical probe can be any probe (e.g., a catheter or surgical probe) that can be placed within the body of a patient. The medical probe further includes a plurality of temperature sensors that are carried by the distal end of the elongate member. Each of the temperature sensors can be digital, in which case, it may conveniently be embodied in an integrated circuit that is configured for outputting digital data representative of a measured temperature. Alternatively, each of the temperature sensors can be analog, in which case, it may be embodied in a thermistor, thermocouple, resistance temperature detector (RTD), or other analog device, that is configured for outputting analog data representative of a measured temperature.

The medical probe further includes a common electrical bus carried by the elongate member. The common electrical bus defines two or more electrical paths, each of which is coupled to the plurality of temperature sensors. By way of nonlimiting example, the two or more electrical paths can comprise three electrical paths represented by respective data, ground, and power lines. Alternatively, power can be parasitically obtained from the data line, in which case, only two electrical paths are needed. The common electrical bus can be embodied in any suitable circuit, e.g., bifilar wire, trifilar wire, flex circuit, or flex circuit/wire hybrid. Each electrical path can be formed of a single wire or trace to which the temperature sensors are connected, or alternatively, can be formed of several wires or traces connected between the temperature sensors in a daisy chaining fashion. In the preferred embodiment, the medical probe includes a handle mounted to the proximal end of the elongate member. The handle includes an interface for connecting the two or more electrical paths to a cable that provides a connection between the medical probe and a console, such as an ablation power generator.

By using a common electrical bus, temperature sensor data from all of the temperature sensors can be conducted within the medical probe using a minimal number of electrical paths. The common electrical bus may extend through the elongate member, directly connecting to the temperature sensors, in which case, the number of electrical paths extending through the medical probe, as well as the connecting cable, can be reduced. Alternatively, the common electrical bus may be located at the proximal end of the medical probe, and indirectly coupled to the temperature sensors through a second electrical bus, in which case, the number of electrical paths extending through the connecting cable can be reduced.

In the preferred embodiment, the medical probe is an ablation probe that includes one or more electrodes carried by the distal end of the elongate member. In this case, the temperature sensors may be located adjacent the electrodes to provide temperature measurements of the tissue during the ablation process. By way of nonlimiting example, the one or more electrodes can be embodied in a segmented electrode, an electrically conductive balloon electrode, a microporous balloon electrode, or a balloon activated splined electrode assembly. If segmented, the electrodes can be, e.g., rigid conductive ring electrodes, spiral coil electrodes, ribbon electrodes, and printed-on electrodes. The one or more electrodes can also comprise a tip electrode. In an ablation probe, the temperature sensors are preferably disposed between the corresponding electrodes and elongate member in contact with the electrodes. Alternatively, the profile of the medical probe can be further reduced by mounting the temperature sensors in beveled openings formed within the corresponding electrodes and arranged therewith in a flush manner.

In accordance with a second aspect of the present inventions, a temperature sensor subassembly comprises a plurality of temperature sensors, and a common electrical bus having two or more wires, each of which is coupled to the plurality of temperature sensors. In the preferred embodiment, the two or more wires are laser stripped to expose attachment points for the plurality of temperature sensors. The temperature sensor subassembly can be embodied in any suitable circuit, e.g., bifilar wire, trifilar wire, flex circuit, or flex circuit/wire hybrid. Each of the temperature sensors can be digital, in which case, it may conveniently be embodied in an integrated circuit that is configured for outputting digital data representative of a measured temperature. Alternatively, each of the temperature sensors can be analog and associated with multiplexing circuitry, in which case, it may be embodied in a thermistor, thermocouple, resistance temperature detector (RTD), or other analog device, that is configured for outputting analog data representative of a measured temperature. The temperature sensor subassembly can be utilized in any assembly or system that requires a multitude of adjacent temperature sensors. Such assembly may include, but is not limited to, medical probes.

In accordance with a third aspect of the present inventions, a medical probe comprises an elongate member, and one or more temperature sensor subassemblies carried by the elongate member. Each of the one or more temperature sensor subassemblies comprises a plurality of temperature sensors and a common electrical bus connected to the plurality of temperature sensors. The temperature sensor subassemblies can be variously configured on the elongate member. By way of nonlimiting example, a single temperature sensor subassembly can extend along one side of the elongate member. In another embodiment, two temperature sensor subassemblies can extend along opposite sides of the elongate member. In still another embodiment, a single temperature assembly can extend along the elongate member in a spiral fashion. In yet another embodiment, a temperature assembly can be in the form of a ring temperature assembly circumferentially extending around the elongate member. To minimize the profile of the medical probe, the one or more temperature sensor subassemblies can be situated in one or more skives formed on the elongate member. In the preferred embodiment, the medical probe is an ablation medical probe that comprises one or more electrodes, in which case, the temperature sensors are located adjacent the one or more electrodes.

In the preferred embodiment, the elongate member comprises an elongate tube with an internal lumen, in which case, each data bus can extend into the internal lumen through orifices made through the elongate tube. Such orifices can be used to simply route each data bus from the exterior of the tube, through the internal lumen back to the proximal end of the medical probe. These orifices can also be used to connect temperature sensors on opposite sides of the elongate member. For example, alternating temperature sensors of one of the temperature sensor subassemblies can be mounted on opposite sides of the tube, with the data bus traversing the internal lumen through orifices formed in the tube on opposite sides thereof. The orifices can also be used to provide slack in each data bus, thereby allowing the medical probe to flex without causing damage to the temperature sensor subassemblies. For example, the plurality of temperature sensors can be mounted on an exterior surface of the tube, and the data bus can be looped inside of the internal lumen through pairs of orifices formed through the tube between the temperature sensors.

In accordance with a fourth aspect of the present inventions, a medical probe comprises an elongate member having a distal end carrying a plurality of digital temperature sensors. Each of the digital temperature sensors is configured to output a digital signal representative of a measured temperature. In this manner, the temperature sensor capability of the medical probe is less susceptible to ambient noise. The digital temperature sensors can be conveniently embodied in integrated circuits. The medical probe further includes a common electrical bus extending through the elongate member, and defining two or more electrical paths, each of which is coupled to the plurality of digital temperature sensors. The two or more electrical paths may define a data line and a ground line. The data line can optionally be used by the digital temperature sensors in a parasitic manner as a power line. In the preferred embodiment, each of the plurality of digital temperature sensors exhibits a unique digital address, thereby allowing temperature data to be individually obtained from each individual digital temperature sensor over the common electrical bus. In the preferred embodiment, the medical probe is an ablation medical probe comprising one or more electrodes, in which case, the plurality of digital temperature sensors are located adjacent the one or more electrodes to facilitate the tissue ablation process.

In accordance with a fifth aspect of the present inventions, a medical probe comprises an elongate member having a distal end carrying a digital temperature sensor. The digital temperature sensor can be conveniently embodied in an integrated circuit. The medical probe further includes an electrical bus extending through the elongate member, and coupled to the digital temperature sensor. In the preferred embodiment, the electrical bus comprises a data line and a ground line. The digital temperature sensor can advantageously use the data line as a power line in a parasitic manner. The medical probe may be an ablation medical probe comprising an electrode, in which case, the digital temperature sensor is located adjacent the electrode.

In accordance with a sixth aspect of the present inventions, a temperature sensing ablation system comprises a medical probe, a cable, and an ablation power generator. The type of ablation power generator that may be implemented with the system include, e.g., a RF ablation power generator, a microwave ablation power generator, an ultrasound ablation power generator, and a cryoablation power generator. The medical probe comprises an elongate member having a proximal end and a distal end. The medical probe further comprises at least one electrode and a plurality of temperature sensors (e.g., digital sensor chips), which are carried by the distal end of the elongate member. The medical probe further comprises ablation leads that extend through the elongate member and are coupled to the at least one electrode. The medical probe further includes a common electrical bus carried by the elongate member. The common electrical bus defines two or more electrical paths, each of which is coupled to the plurality of temperature sensors. The common electrical bus can extend through the elongate member and be connected directly to the temperature sensors, or alternatively, be located within the proximal end of the elongate member, in which case, an intermediate electrical bus can connect the common electrical bus indirectly to the temperature sensors.

The ablation power generator is coupled to the medical probe through the cable. In this respect, the ablation power generator is configured for receiving temperature data from the plurality of temperature sensors, and being configured for controllably transmitting energy to the at least one electrode based on the received temperature data. In the preferred embodiment, the medical probe comprises a handle carried by the proximal end of the elongate member. The handle carries an interface to connect the cable to the ablation leads and common electrical bus.

In accordance with a seventh aspect of the present inventions, an ablation power generator for delivering ablation power to a medical probe is provided. The ablation power generator comprises a power source and temperature control circuitry. The power source is capable of delivering ablation power to ablation elements located on the medical probe, and can take the form of, e.g., an RF power source, cryoablation power source, or ultrasound power source. The temperature control circuitry is designed to communicate with digital temperature sensors located on the probe, and may comprise, e.g., a microprocessor.

The power generator preferably includes an interface that allows the generator to mate with a cable and subsequently to the probe. The interface enables the power generator, and specifically the temperature control circuitry of the power generator, to receive digital data from the interface. In one embodiment, the power generator is configured to communicate with a medical probe that has a plurality of digital temperature sensors. In this embodiment, the power generator includes an interface configured for serially receiving digital data from the plurality of digital sensors, in which case, the temperature control circuitry is designed to receive the digital data from the interface.

In accordance with an eighth aspect of the present inventions, an ablation power generator designed for use with a medical probe having at least one ablation element and a plurality of temperature sensors located on a common data bus is provided. The temperature sensors may be either digital or analog sensors. The power generator is configured to deliver ablation power to the ablation element. The power generator further includes temperature control circuitry that communicates with the temperature sensors located on the common data bus.

These and other aspects of the present invention are described herein in greater detail.

DESCRIPTION OF THE DRAWINGS

FIG. 5b is a side view of the temperature sensor subassembly of FIG. 5a;

FIG. 6a is a bottom view of a digital temperature sensor chip used in the temperature sensor subassembly shown in FIG. 5a;

FIG. 6b is a side view of the digital temperature sensor chip of FIG. 6a;

FIG. 8 is a perspective view of a first preferred embodiment of a probe body incorporating the temperature sensor subassembly of FIG. 5a;

FIG. 10 is a perspective view of a second preferred embodiment of a probe body incorporating the temperature sensor subassembly of FIG. 5a;

FIG. 12 is a perspective view of a third preferred embodiment of a probe body incorporating two of the temperature sensor subassemblies of FIG. 5a;

FIG. 14 is a perspective view of a fourth preferred embodiment of a probe body incorporating two of the temperature sensor subassemblies of FIG. 5a;

FIG. 16 is a perspective view of a fifth preferred embodiment of a probe body incorporating the temperature sensor subassembly of FIG. 5a;

FIG. 17 is a perspective view of a sixth preferred embodiment of a probe body incorporating the temperature sensor subassembly of FIG. 5a;

FIG. 20 is a perspective view of a seventh preferred embodiment of a probe body incorporating the temperature sensor subassembly of FIG. 5a;

FIG. 22 is a perspective view of an eighth preferred embodiment of a probe body incorporating the temperature sensor subassembly of FIG. 5a;

DETAILED DESCRIPTION

In a preferred embodiment, the system of the present invention is applicable to medical probes, such as catheters and surgical probes, that rely on temperature feedback to regulate ablation therapy. To this end, temperature sensors located at the distal end of a probe body communicate temperature measurements of the target tissue to an ablation power generator. Such temperature measurement communication is preferably accomplished digitally to take advantage of the benefits disclosed herein, such as noise resistance and simplicity of manufacture, but can alternatively be accomplished through analog means. Multiple temperature sensors are preferably connected together in parallel at the distal end of the probe to reduce the number of wires between the temperature sensors and the power generator. Alternatively, the multiple temperature sensors are connected together in parallel at an interface located in the handle of the probe to reduce the number of wires between the handle of the probe and the power generator. Electrodes are carried on the distal end of the probe body, and are in operative contact with the sensors, in order to control ablation energy from the power generator to form lesions on the target tissue.

General System Structure

Figure 1:
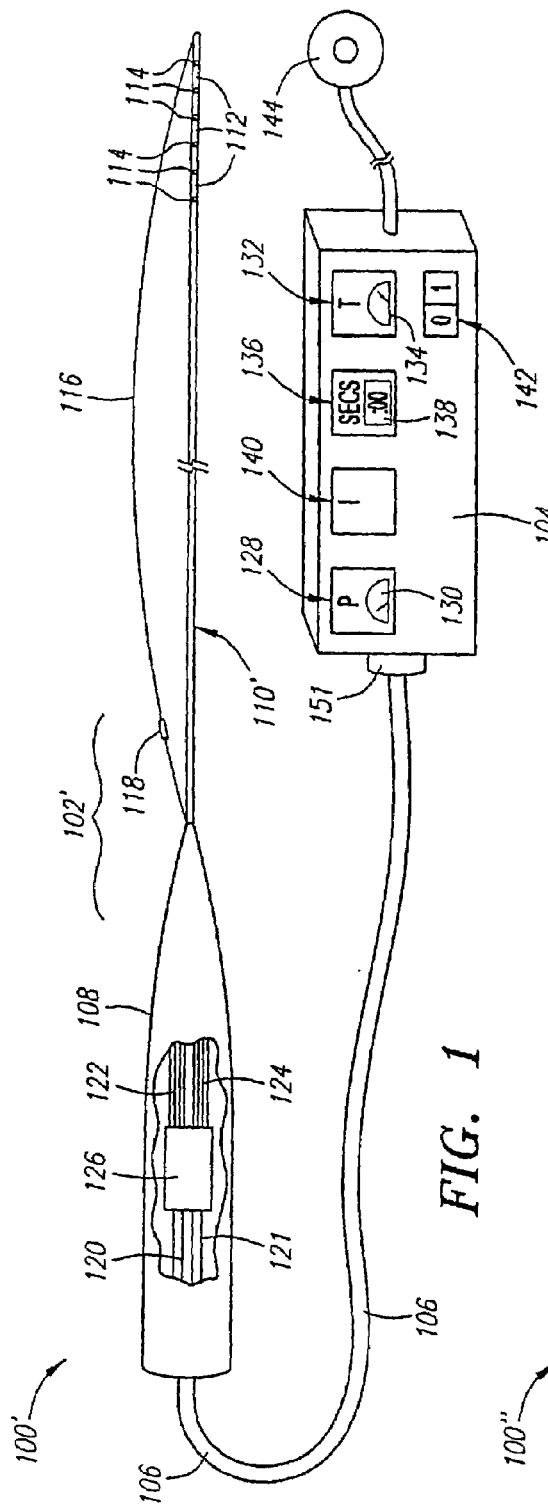
FIG. 1 illustrates an embodiment of a catheter-based system constructed in accordance with the present inventions.

With reference to FIG. 1, a catheter-based system 100' constructed in accordance with a preferred embodiment of the present inventions is illustrated. The system 100' includes a catheter 102' and a power generator 104, which are connected together through a cable 106. The catheter 102' comprises a handle 108 and an elongated catheter body 110'. The catheter body 110' has a proximal end, which connects to the handle 108 in a suitable manner, and a distal end, which carries a plurality of segmented electrodes 112 (in this case, three), which are designed to deliver ablation energy to the target tissue. As will be described in further detail below, the number and type of electrodes carried by the catheter body 110' may vary. The distal end of the catheter body 110' further carries a plurality of corresponding temperature sensors 114 (in this case, six), which operate in conjunction with electrodes 112 to provide temperature measurements of the body tissue to the power generator 104 during the ablation process. Preferably, to ensure accuracy in measurement, the sensors 114 are configured such that they are as close as possible to the tissue being heated, as will be described in further detail below.

Although the electrodes 112 are shown as segmented electrodes, the present inventions should not be so limited. For example, a single tip electrode, which will be discussed in further detail below, can be employed with the present inventions. Other electrodes, such as electrically conductive balloon electrodes, microporous balloon electrodes, and balloon activated splined electrode structures, can also be employed with the present inventions. Preferred embodiments of electrically conductive balloon electrodes and corresponding methods of manufacture are described in U.S. Pat. No. 5,891,136 to McGee et al., filed Apr. 12, 1996, which is fully and expressly incorporated herein by reference. Preferred embodiments of microporous balloon electrodes and corresponding methods of manufacture are described in U.S. Pat. No. 5,840,076 to Swanson et al., filed Apr. 12, 1996, which is fully and expressly incorporated herein by reference. Preferred embodiments of balloon activated splined electrode structures are described in copending U.S. application Ser. No. 09/032,226 to Whayne et al., filed Feb. 27, 1998, which is fully and expressly incorporated herein by reference.

In the embodiment illustrated in FIG. 1, a pull wire 116 and pull wire manipulator 118 are provided, enabling an operator of the catheter 102' to flex the catheter body 110' in order to optimally position the catheter body 110' within a body cavity. The ends of the pull wire 116 are respectively connected to the distal tip of the catheter body 110' and handle 108. Alternatively, the catheter 102' can be provided with a steering mechanism, such as the one disclosed in U.S. Pat. No. 5,254,088 to Lundquist et al., which is fully and expressly incorporated herein by reference. The catheter body 110' is preferably made of an extruded polymeric, electrically nonconductive material such as polyethylene or polyurethane, allowing the catheter body 110' to be flexed in order to assume various curvilinear shapes. Preferably, a support element (not shown) is situated within the catheter body 110' to provide further rigidity, thereby allowing the catheter body 110' to be controllably flexed to conform with the tissue targeted for ablation.

The cable 106 enables the catheter 102' to interact with the power generator 104 via plugs (not shown), and extends from the proximal end of the handle 108 of the catheter 102'. In this embodiment, the cable 106 electrically connects with proximal ablation leads 120 and a proximal common data bus 121 located within the handle 108. In the preferred embodiment, the leads 120 and bus 121 located within the handle 108 are formed from the distal ends of wires within the cable 106, but may alternatively be separate from the cable, in which case, the proximal ends of the cable wires can be suitably connected to the leads 120 and bus 121. The catheter body 110' further comprises distal ablation leads 122, which extend the length of the catheter body 110', connecting distally to the electrodes and proximally to the proximal ablation leads 122 via a probe interface 126. The catheter also comprises a distal common data bus 124, which also extends the length of the catheter body 110', connecting distally to the temperature sensors 112 and proximally to the proximal common data bus 121 via the interface 126. The interface 126 can be embodied in any suitable device that enables a connection between wires, e.g., a printed circuit board or a connector. The arrangement of the leads 120, 122 and the busses 121, 124 will be described in further detail below.

The ablation power generator 104 is preferably a radio frequency (RF) generator. Any suitable ablation power generator 104 may be utilized, however, including, e.g., a microwave generator, an ultrasound generator, a cryoablation generator, and a laser or other optical generator. In one embodiment, the ablation power generator 104 delivers radio frequency energy to the catheter 102' in a controlled manner. To this end, the power generator 104 comprises a microprocessor 146 (shown in FIGS. 3 and 4), which controls the amount of ablation energy delivered by a power source 148 (also shown in FIGS. 3 and 4) to the electrodes 112, and a generator interface 151 for facilitating the input of temperature sensing data from the temperature sensors 114 into the microprocessor 146. The microprocessor 148, power source 148, and generator interface 151 will be described in further detail below. The cable 106 provides a connection between the probe interface 126 of the probe 102 and the generator interface 151 of the power generator 104.

A physician or other operator may operate the power generator 104 to controllably deliver ablation energy to targeted tissue. Specifically, the power generator 104 comprises setpoint parameters, which can be adjusted when the power generator 104 is in standby mode. The setpoint parameters include, among others, the magnitude of the ablation power delivered to the tissue, the desired tissue temperature, and the duration of ablation power delivery.

To this end, the ablation power delivered by the power generator 104 is set using a power control input 128. The actual ablation power delivered by the power generator 104 is reported by a power meter 130. During ablation energy delivery, the power generator 104 adjusts power output to maintain an actual measured temperature at the temperature setpoint. The desired temperature to which the ablated tissue is exposed is set using a temperature control input 132. The actual temperature to which the ablated tissue is exposed, which is obtained from the temperature sensors 114, is reported by a temperature gauge 134. In the preferred embodiment, the sensors 114 are designed to automatically convert the temperature data to an appropriate temperature format prior to transmission of the data to the power generator 104. Alternatively, the microprocessor converts temperature data received from the sensors 114 into an appropriate temperature measurement, such as Celsius or Fahrenheit. The power delivered to the sensors 114 preferably results in a relatively low current level, e.g., below 10 $\mu$A, in order to avoid delivering current that would prove dangerous to the patient.

When the power generator 104 is used with a catheter 102', the desired duration of ablation power may be controlled. The desired duration of ablation power applied is set using a timer 136. A counter 138 tracks the elapsed time from initial delivery of ablation power to the tissue, and counts from zero to the setpoint duration. When loss of contact with tissue is detected, the counter 138 stops. Contact between the electrodes 112 located on the catheter body 110' is measured with an impedance meter 140. The power generator 104 includes an ablation power control button 142, which places the power generator 104 in deliver mode when depressed in a power "on" orientation. When in the deliver mode, the power generator 104 delivers ablation energy to the tissue in contact with the electrodes 112 until the count displayed by the counter 138 reaches the setpoint duration or until the power control button 142 is depressed into a power "off" orientation.

In the illustrated embodiment, the system 100' operates in a monopolar mode. To properly operate in this mode, the system 100' includes a skin patch electrode that serves as an indifferent second electrode 144 separate from the catheter 102' and its electrodes 112. In use, the indifferent electrode 144 is attached to the patient's back or other exterior skin area. When operated in the monopolar mode, ablating energy is emitted between one of the electrodes 112 and the indifferent electrode 144. Alternatively, the system 100' is operated in a bipolar mode, in which case, ablating energy is emitted between two of the electrodes 112, thereby eliminating the need for an indifferent electrode 144 separate from the catheter 102'.

Further details on the use and structure of an RF power generator are disclosed in U.S. Pat. No. 5,383,874 to Jackson, et al., filed Nov. 13, 1992, which is expressly and fully incorporated herein by reference.

Figure 2:
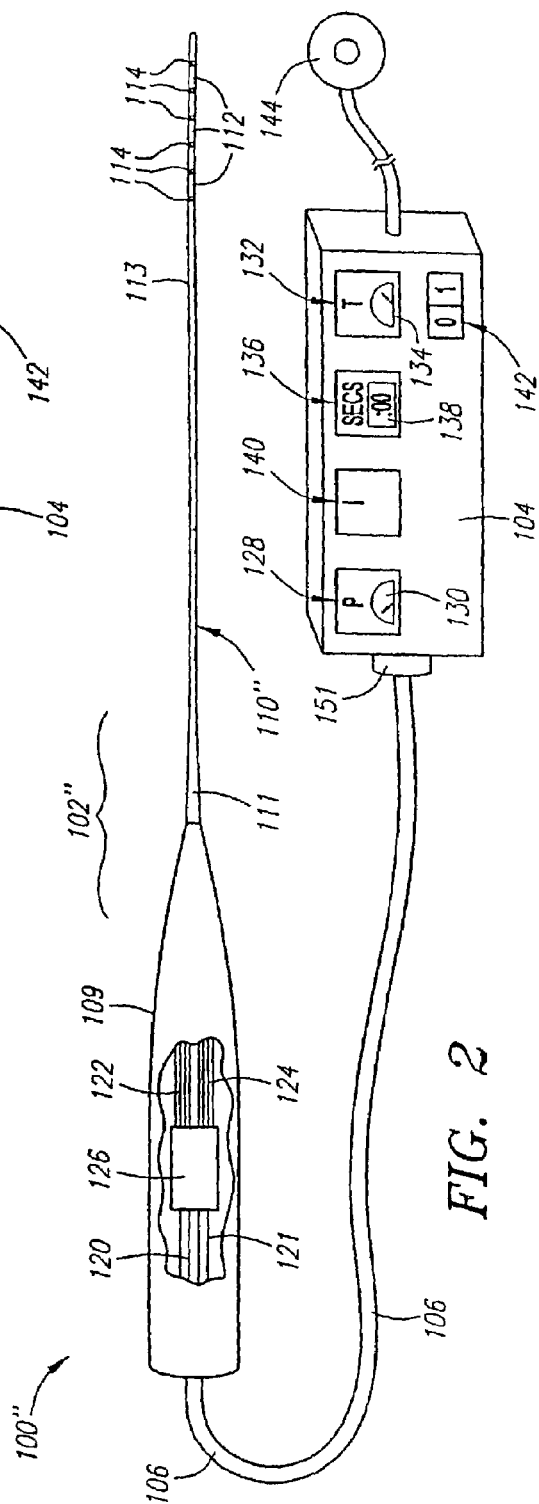
FIG. 2 illustrates a surgical probe-based system constructed in accordance with the present inventions.

With reference to FIG. 2, a surgical probe-based system 100" constructed in accordance with the present inventions is described. The surgical probe system 100" is similar to the catheter-based system 100' described above, and to the extent that the components of both systems are similar, identical reference numbers have been assigned. The system 100" differs from the system 100' in that it includes a surgical probe 102", rather than a catheter 102'. The surgical probe 102" includes a surgical probe body 110" and a handle 109. The surgical probe body 110" includes a relatively short, relatively stiff shaft 111, on which the handle 109 is suitably mounted, and a distal section 113. The shaft 111 may be from about 4 inches to 18 inches in length and is preferably about 6 to 8 inches. The distal section 113 may be from about 1 to 10 inches in length and is preferably about 4 to 6 inches. The surgical probe system 100" is particularly useful because it can be easily inserted into the patient during open heart surgery or through an introducing port such as a trocar. Additional information concerning surgical probes may be found in U.S. application Ser. No. 09/072,872, filed May 5, 1998, which is expressly and fully incorporated herein by reference.

Interaction between the surgical probe 102" and the ablation power generator 104 is similar to that described above between the catheter 102' and the ablation power generator 104 with the exception that the duration of ablation power may not be set when using the surgical probe 102". Therefore, for purposes of brevity, such operation will not be repeated. Hereinafter, all references will be to a medical probe system 100, which encompasses both the catheter system 100' and the surgical probe system 100", as well as any other types of medical probe based systems. For example, all further references to the medical probe 102 encompass both the catheter 102' and the surgical probe 102". Likewise, all further references to the probe body 110 encompass both the catheter body 110' and the surgical probe body 110".

Common Data Busses

Figure 3:
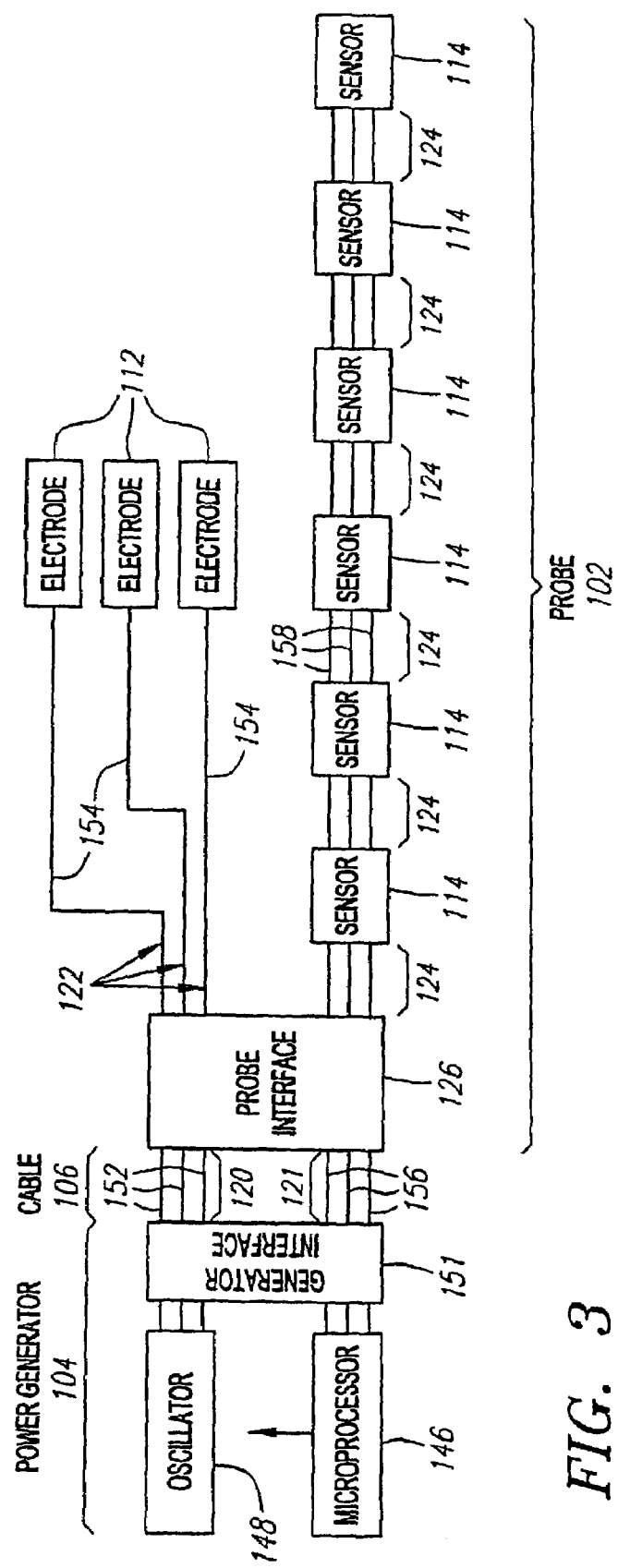
FIG. 3 is a schematic diagram of a preferred embodiment of an electrical circuit implemented in a medical probe system, wherein digital temperature sensors are connected to a power generator through common electrical paths located in the medical probe and connecting cable.

Turning to FIG. 3, a schematic illustration of the electrical system in the medical probe system 100 is shown. In this embodiment of the electrical system, a microprocessor 146 is shown coupled to the plurality of temperature sensors 114 through the proximal common data bus 121, the probe interface 126, and the distal common data bus 124, thereby allowing the microprocessor 146 to receive temperature data from the temperature sensors 114.

As will be described in further detail below, the temperature sensors 114 are preferably digital temperature sensors, each of which is embodied in an integrated circuit. As a result, the microprocessor 146 can receive digital temperature data via the generator interface 151 without the need to implement interfacing analog-to-digital circuitry within the power generator 104.

The use of digital temperature sensors also provides for an improved noise performance. Digital temperature sensors can provide greater immunity to electrical noise compared to analog temperature sensors. With analog sensors, even small induced voltages can result in variability of the measured temperature. Thermocouples are particularly susceptible to electrical noise, due to their tiny microvolt-level output. Filtering of the analog signal is possible, but it adds expense and complexity to the measurement circuit, and can never completely eliminate the noise. Digital sensors, on the other hand, can be completely error-free as long as the noise is lower in amplitude than the logic threshold which distinguishes logic "0" from logic "1" (over 2 volts, in the case of TTL logic). Even when transient noise exceeds the logic threshold, there are standard digital techniques for serial communication (such as parity or cyclic redundancy codes) that can be used to detect and correct (or retry) garbled temperature readings.

The power source 148, such as an oscillator, is shown coupled to the plurality of electrodes 112 through the proximal ablation leads 120, generator interface 151, probe interface 126, and distal ablation leads 122, thereby allowing the power source 148 to deliver ablation energy to the electrodes 112. The microprocessor 146 controls the ablation energy output from the power source 148 based on the temperature data obtained from the temperature sensors 114.

As in typical fashion, the distal ablation leads 122 includes a wire 154 for each electrode 112 (in this case, three pairs), and the proximal ablation leads 120 likewise includes a wire 152 for each electrode 112 (in this case, three pairs). The distal common data bus 124, however, defines three electrical paths, each of which is connected to all three temperature sensors 114. Specifically, the distal common data bus 124 includes three wires 158, which connect the temperature sensors 114 in parallel. In the preferred embodiment, each of the three wires 158 is a single wire on which the temperature sensors 114 (in this case six) are connected. Alternatively, each of the three wires 158 are daisy chained, i.e., each includes a plurality of wires connected in series through the internal circuitry of the temperature sensors 114. Either way, the distal common data bus 124 defines three separate electrical paths, which includes a data line, ground line, and power line.

Optionally, as will be described in further detail below, the temperature sensors 114 are configured to parasitically use the data line as a power line, in which case, one electrical path can be eliminated from the distal common data bus 124. This has the added advantage of obviating the need to run DC power through the medical probe, which would otherwise pose a danger to the patient during heart tissue ablation. Thus, it can be seen that the number of electrical paths contained in the distal common data bus 124, as compared to prior art implementations, has been reduced to two or three, thereby reducing the number of wires contained within the medical probe 102. Accordingly, the profile of the catheter body 110 is minimized, and the placement of multiple temperature sensors 114 on the distal end of the medical probe 102 is facilitated, since the reduced number of wires occupies a correspondingly reduced area within the lumen of the probe body 14. Additionally, the proximal common data bus 121 defines two or three electrical paths (data, ground, and power), represented by wires 156, which are respectively connected to the wires 158 of the distal common data bus 124 through the probe interface 126. As a result, the number of wires contained in the cable 106 is also reduced.

Figure 4:
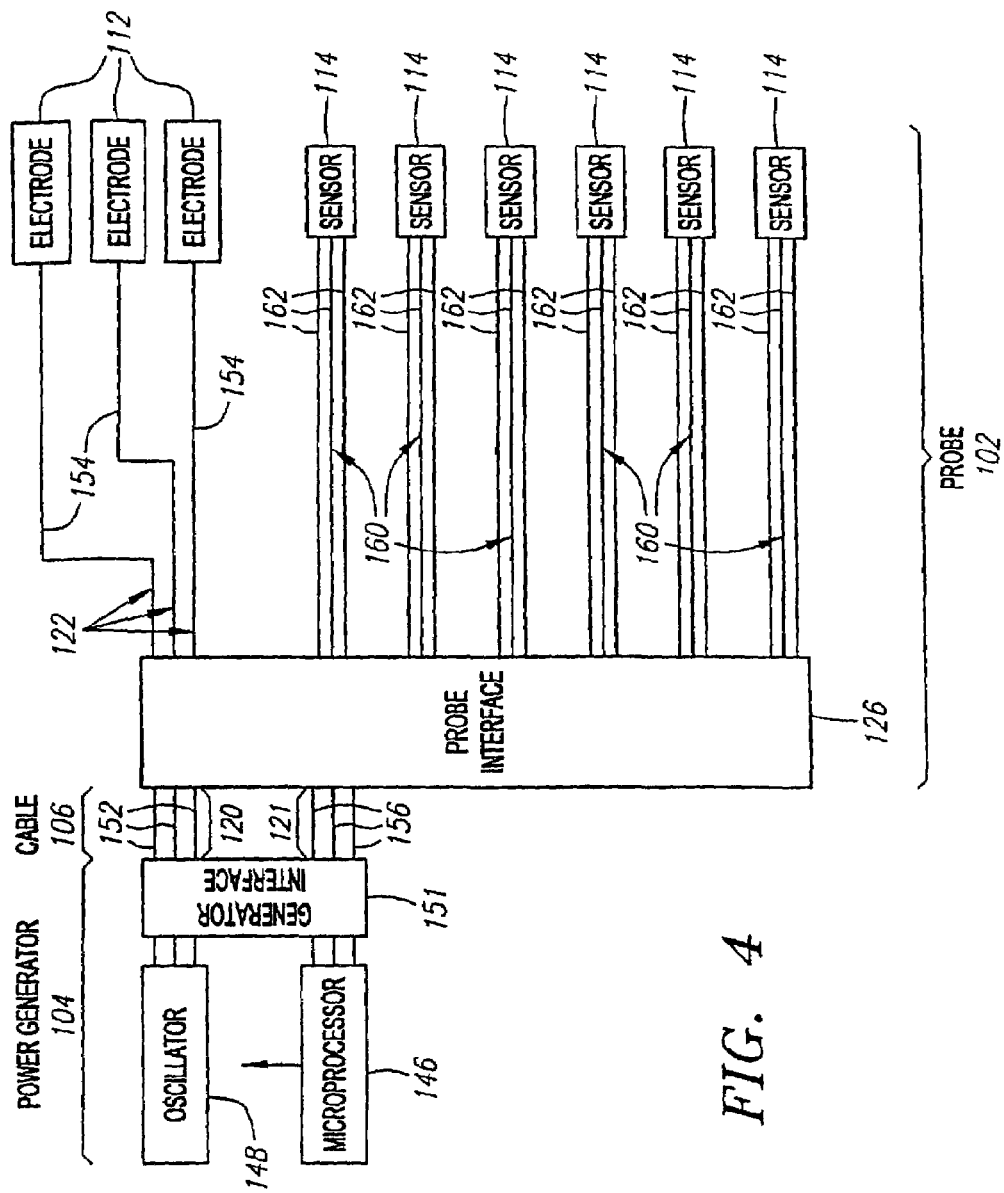
FIG. 4 is a schematic diagram of a preferred embodiment of an electrical circuit implemented in a medical probe system, wherein digital temperature sensors are connected to a power generator through common electrical paths located only in the connecting cable.

Turning now to FIG. 4, an alternative electrical system of the medical probe system 100 is illustrated. This electrical system is similar to the one described with the respect to FIG. 3, with the exception that the sensors 114 are connected to the interface 126 through a distal data bus 160 that includes separate electrical paths for each temperature sensor 114. Specifically, the distal data bus 160 includes three trios of wires 162, which connect the temperature sensors 114 independent from each other. In this manner, the distal data bus 160 is not common, as with the distal common data bus 124 described above, but is rather discrete. The proximal common data bus 121, however, still includes only three electrical paths for all temperature sensors 114, and specifically, the two or three wires 156, which connect to the wires 162 through the probe interface 126. That is, the data line, ground line, and power line (if present) of the proximal common data bus 121 connects to the three data lines, three ground lines, and three power lines (if present) of the distal data bus 160. Thus, in comparison to the embodiment illustrated in FIG. 3, only the cable 106 of this embodiment includes a reduced number of wires.

Temperature Sensor Controller

As seen in FIG. 3 and FIG. 4, and as previously described above, the power generator 104 includes temperature sensor controller circuitry that preferably is implemented by the microprocessor 146. The temperature control circuitry is capable of directly processing digital input and output signals from and to the sensors 114 via the generator interface 151. Thus, the need for separate analog-digital converters or separate signal conditioners is eliminated. A key feature of the temperature controlling function of the power generator 104 is that the basic design of the temperature controller circuitry that is necessary to send and receive direct digital output and input via the generator interface 151 remains the same regardless of the number of temperature sensors 114 located on the probe 102 that are in communication with the power generator 104. This also enables the same basic power generator 104 to control various probes that include different numbers of sensors without necessitating a change in the design of the temperature control circuitry of the generator 104. To accomplish this function, the microprocessor 146, in the embodiment illustrated in FIG. 3 and FIG. 4, automatically polls the probe 102 in order to determine the number of sensors 114 located on the probe 102. For a detailed description of the electrical and software interface operations of the sensors 114, see Dallas Semiconductor, Book of iButton Standards, Chapters 4 and 5, which is fully and expressly incorporated herein by reference.

Digital Temperature Sensors

As briefly discussed above, each temperature sensor 114 preferably comprises a digital temperature sensor chip 114' (shown in FIGS. 6a and 6b), which is capable of sensing temperature data and outputting the temperature data directly in a digital format. One advantage of utilizing digital temperature sensor chips 114' is that the transmission of digital data is relatively error-free when compared to analog data transmission. Therefore, the use of digital temperature sensor chips 114' will reduce the possibility of errors that might otherwise develop if analog sensors are utilized.

Temperature sensing chips of the preferred variety may be obtained from Dallas Semiconductor (Dallas, Tex.). Unlike traditional integrated circuits intended for assembly on printed circuit boards, which are too large for use in catheters or probes, the chips 114' used with the present invention, such as those available from Dallas Semiconductor, are available in a chip scale package and are only slightly larger than a silicon chip.

The chips 114' are designed to communicate with the microprocessor 146 of the power generator 104 through the use of single input/output bits of the microprocessor 146. In this regard, each sensor chip 114' has a unique digital address associated with it, allowing the microprocessor 146 to separately and individually read temperature data from the parallel configured chips 114'. This communication scheme employs a common read/write line, i.e., each sensor chip 114' individually communicates digital data to the microprocessor 146 by individually utilizing the data line during "read slots" assigned by the microprocessor 146.

To sense and measure temperature, the digital temperature sensor chips 114' count the temperature varying output of an on-chip oscillator. In the preferred embodiment, the sensor chip 114' converts the count directly into degrees. Alternatively, the sensor chip 114' transfers the count to the microprocessor 146, which performs the conversion of the count to degrees. When addressed individually, and commanded by the microprocessor 146, each sensor chip 114' communicates its own sense temperature reading via the common data busses 121 and 124. Thus, each sensor chip 114' may be polled separately at a rate that is only limited by the total number of chips 114' connected to the distal common data bus 124. To increase the temperature sensing speed, polling can be limited to only those chips 114' on or near electrodes 112 that are actually performing ablation at the time the temperature is measured. Alternatively, polling speed is increased by dividing the common data busses 121 and 124 into electrically separate branches controlled by bus switches specifically designed to compartmentalize temperature readings from different groups of chips 114'. In this case, the bus switch can be located either in the handle 108 of the medical probe 10, the ablation power generator 104, or the distal end of the medical probe 102.

The digital temperature sensor chips 114' optionally operate using a parasitic power arrangement that reduces the number of wires required to operate the sensor chips 114' from three to two. For example, the parasitic power arrangement allows a multiple number of sensors to operate using a single data wire and a single ground wire. The sensor chips 114' draw their operating power from the common data line so that a separate power supply wire is not required for the operation of the sensor chips 114'.

The digital temperature sensor chips 114' currently available for use with the system are slightly larger than either conventional thermocouples or thermistors, with dimensions of approximately 0.03"×0.0525"×0.0765". The size of the sensor chips 114' capable of implementation within the system may be reduced by eliminating unnecessary features on the sensor chips 114' that the system 100 does not utilize, including high and low temperature alarm memories. A redesign of the sensor chips 114' to a longer and narrower configuration would also facilitate the incorporation of the sensor chips 114' into a catheter or probe system. Additionally, new semiconductor manufacturing processes may result in a 50% or more reduction in the volume of the sensor chips 114'.

The digital temperature sensor chips 114' may also be implemented with filtering circuitry designed to specifically reject interference from the ablation power generator 104. For example, analog notch filters or digital signal processing may be utilized to reject the noise emanating from the ablation power generator 104. The incorporation of filtering would enable the system to operate with greater efficiency since an increased level of ambient noise would be prevented from interfering with the operation of the sensors.

Temperature Sensor Subassemblies

Figure 5A:
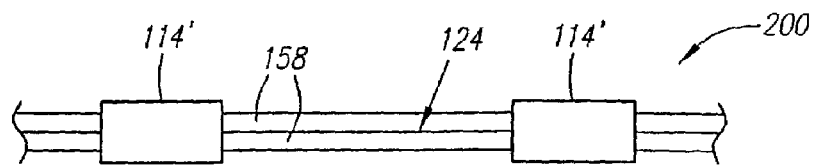
FIG. 5a is a top view of an embodiment of a temperature sensor subassembly constructed in accordance with the present inventions.
Figure 5B:
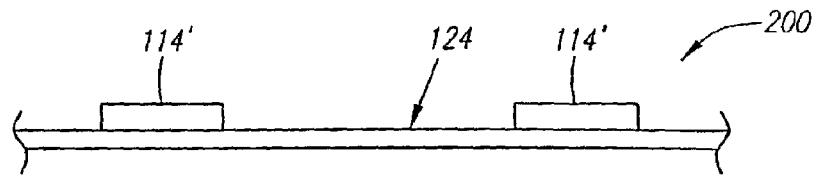

Turning to FIGS. 5a and 5b, a temperature sensor subassembly 200 constructed in accordance with a preferred embodiment of the present inventions is illustrated. The temperature sensor subassembly 200 can be implemented in any assembly that requires multiple temperature sensors in close proximity to each other. The temperature sensor subassembly 200 includes two common electrical paths to which temperature sensors 114 are connected. Specifically, the subassembly 200 comprises a combination of the temperature sensors 114 and the common data bus 124. In the illustrated embodiment, the distal common data bus 124 comprises two wires 158 (data/power and ground), and the temperature sensors 114 are embodied in digital temperature sensor chips 114'.

The data bus 124 can be embodied in any suitable form, e.g., discrete insulated wires, bifilar wires, trifilar wires (in the case where three wires 158 are needed), or flex circuits (in which case, the wires 158 will be traces), that provide a common electrical path for the sensor chips 114'. Should the distance traveled by the data bus 124 exceed a couple of feet, the use of bifilar wire is preferred. Thus, it can be seen that the use of the temperature sensor subassembly 200 allows a multiple number of sensor chips 114' to be connected in parallel using the same two or three wires, or the same two or three traces if the data bus 124 is embodied in a flex circuit. It should be noted that although the subassembly 200 is illustrated with two wires 158, to accommodate other function, it can include three or more wires 158 without straying from the principles taught by this invention.

Figure 5C:
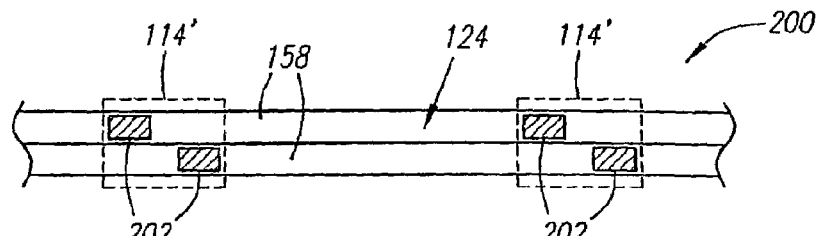
FIG. 5c is a top view of the temperature sensor subassembly of FIG. 5a, particularly showing exposed regions on which the temperature sensors are mounted.
Figure 6A:
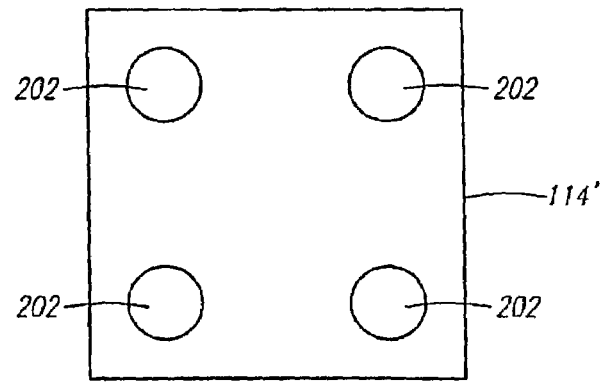
Figure 6B:
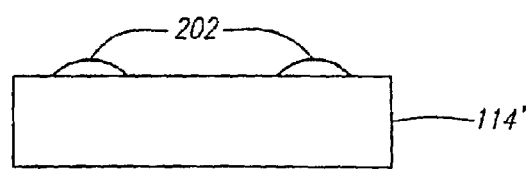

The sensor chips 114' are attached to the wires 158 of the data bus 124 through the use of solder, conductive adhesive, or ultrasonic bonding of metal or solder. Specifically, as illustrated in FIG. 5c, the data bus 124 comprises areas 202 where the wires 158 have been exposed through the insulation using suitable means such as laser etching. For purposes of illustrating the exposed area 202, the sensor chips 114' are shown in phantom. Once all of the exposed areas 202 are formed on the data bus 124, the terminals of the sensor chips 114' are then suitably connected to the exposed areas 202. Specifically, FIGS. 6a and 6b illustrate a sensor chip 114', which uses solder bumps 184 for electrical connection. In this case, the sensor chips 114' are placed on the data bus 124, with two of the diagonal solder bumps 184 of each sensor chip 114' aligned with the corresponding exposed areas 202 of the data bus 124. Of course, the number and specific solder bumps 184 that will be aligned with corresponding exposed areas 202 of the data bus 124 will depend on the particular design of the sensor chip 114 and the functionality that is to be imparted to the subassembly 200. Integral connection between the sensor chips 114' and the data bus 124 is achieved by placing the subassembly 200 through a solder flow process.

Figure 7:
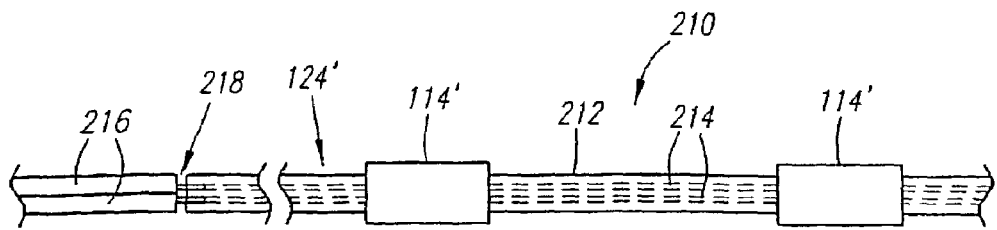
FIG. 7 is an embodiment of a flex/circuit hybrid temperature sensor subassembly constructed in accordance with the present invention.

Turning to FIG. 7, a temperature sensor subassembly 210 constructed in accordance with alternative preferred embodiment of the present inventions is illustrated. Like the temperature sensor subassembly 200 described above, the temperature sensor subassembly 210 is shown having two electrical paths to which temperature sensors 114 are connected. The subassembly 210, however, includes a common data bus 124', which is formed of a hybrid flex circuit/wire arrangement. Specifically, the distal end of the data bus 124' comprises a flex circuit 212 with electrical traces 214 (shown in phantom) on which the sensor chips 114' are mounted. This can be accomplished in a manner similar to that used above to mount the sensor chips 114' on the data bus 124, with the solder bumps 202 of each sensor chip 114' being connected to a corresponding bond pad (not shown) on the flex circuit 212. The proximal end of the data bus 124' is embodied in a wired arrangement, such as bifilar or trifilar wiring, which is shown as wires 216. The wires 158 can be suitably spliced onto the electrical traces 214 of the flex circuit 212 at connection 218, which is preferably located as close to the sensor chips 114' as possible. In this manner, the flex circuit 212 is used to conveniently mount the sensor chips 114' to the data bus 124', while simultaneously lowering costs by using the less expensive wiring 216 along most of the length of the subassembly 210.

Medical Probes with Temperature Sensor Subassemblies and Segmented Electrodes

Various embodiments for the arrangement of one or more temperature sensor subassemblies 200 within the probe body 110 will now be described in detail. The different arrangements of temperature sensor subassemblies 200 will be differentiated by different reference numbers for each corresponding probe body 110, e.g. 110(1), 110(2), etc.

Figure 8:
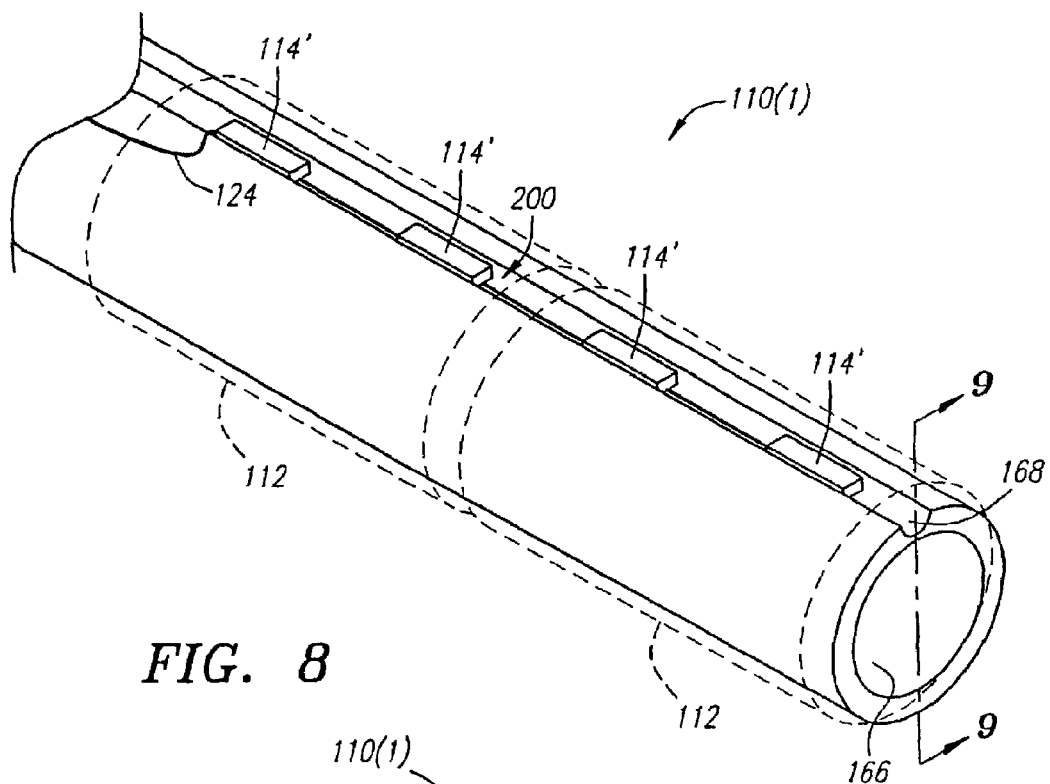
Figure 9:
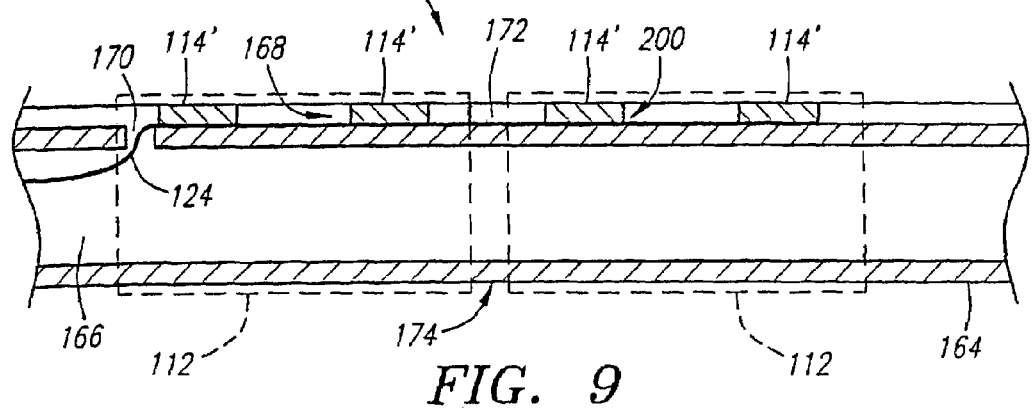
FIG. 9 is a longitudinal sectional view of the probe body of FIG. 8 taken along the line 9—9.

Referring to FIGS. 8 and 9, a probe body 110(1) constructed in accordance with a preferred embodiment of the present inventions is described. The probe body 110(1) comprises an elongate tube 164 through which a lumen 166 extends. The tube 164 is made of a polymeric, electrically nonconductive material, like polyethylene or polyurethane. The tube 164 carries the electrodes 112, as well as a single temperature sensor subassembly 200, which extends along one side of the tube 164. In this manner, the probe body 110(1) exhibits a temperature sensing capability on one side, preferably the side that is used to ablate the tissue. The probe body 110(1) is configured such that it exhibits a reduced profile. To this end, the subassembly 200 is situated within an axial skive 168 (best shown in FIG. 8) formed along one side of the tube 164. The skive 168 may be continuous along the entire length of the tube 164. Alternatively, the skive 168 may comprise a series of separate, discrete skives located along selected locations of the tube 164. In the embodiment where the skive 168 comprises a series of separate, discrete skives, the skives preferably are located where a subassembly 200 is located. As a result of the placement of the subassembly 200 within a skive 168, the thickness of the sensor chips 114' do not add, or add minimally, to the profile of the probe body 110(1).

The electrodes 112, which are preferably composed of a conductive and biocompatible material, such as platinum-iridium or gold, are suitably mounted on the tube 164. In the illustrated embodiment, the electrodes 112 are rigid and are composed of solid rings pressure fitted about the tube 164. The electrodes 112 are separated a distance from each other, providing the probe body 110(1) with nonconductive flexible regions 174 therebetween. In this manner, the distal end of the probe body 110(1) can be flexed in any direction, allowing the electrodes 112 to be brought into intimate contact along the tissue surface regardless of the tissue surface contour. Alternatively, the electrodes 112 can be flexible themselves, and may be composed of closely wound spiral coil electrodes or ribbon electrodes, such as the types disclosed in U.S. Pat. No. 5,582,609 to Swanson et al., filed Aug. 8, 1994, and which is fully and expressly incorporated herein by reference. More alternatively, the electrodes 112 can be composed of printed-on conductive ink and regenerated cellulose, which is formed by disposing bands of conductive, flexible ink over the tube 164, and then disposing a protective coating of regenerated cellulose over the conductive bands. A preferred methodology for forming such electrodes is disclosed and described in co-pending U.S. patent application Ser. No. 08/879,343, filed Jun. 20, 1997, which is fully and expressly incorporated herein by reference.

As illustrated, the digital temperature sensor chips 114' are mounted within the skive 168 between the outer surface of the tube 164 and the inner surface of the electrodes 112, with the bottom side of the sensor chips 114' facing the tube 164 and the top side of the sensor chips 114' facing the electrodes 112. Preferably, the sensor chips 114' are in contact with the electrodes 112, providing a more accurate temperature reading of the tissue during the ablation process. To ensure proper attachment of the data bus 124 to the tube 164, a bonding compound (not shown) is used to secure the data bus 124 to the outside surface of the tube 164. The sensor chips 114' are sealed within the skive 168, by suitably disposing a sealing material 172, such as, e.g., an ultraviolet sensitive adhesive, an epoxy, or any suitable glue, within the skive 168 between the electrodes 112. The data bus 124 extends along the entire length of the skive 168 outside the tube 164, and along the remaining section of the tube 164 within the lumen 166. To this end, an orifice 170 is formed through the wall of the tube 164 at the proximal end of the skive 164, where the data bus 124 is routed from the skive 168 into the lumen 166.

Figure 10:
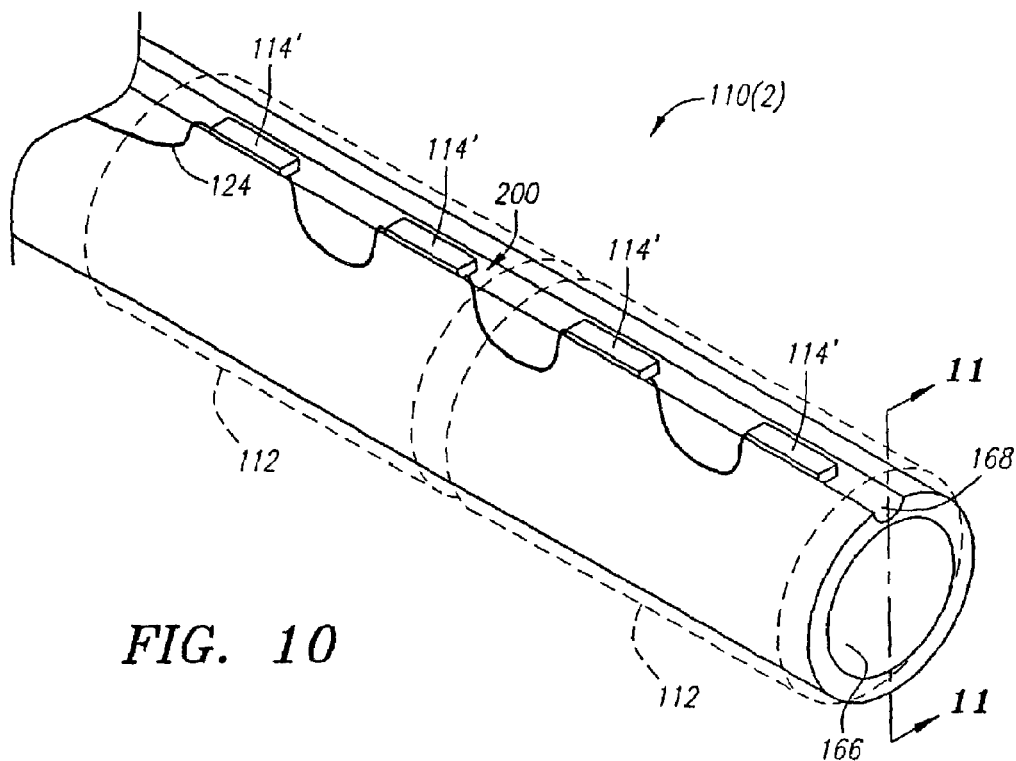
Figure 11:
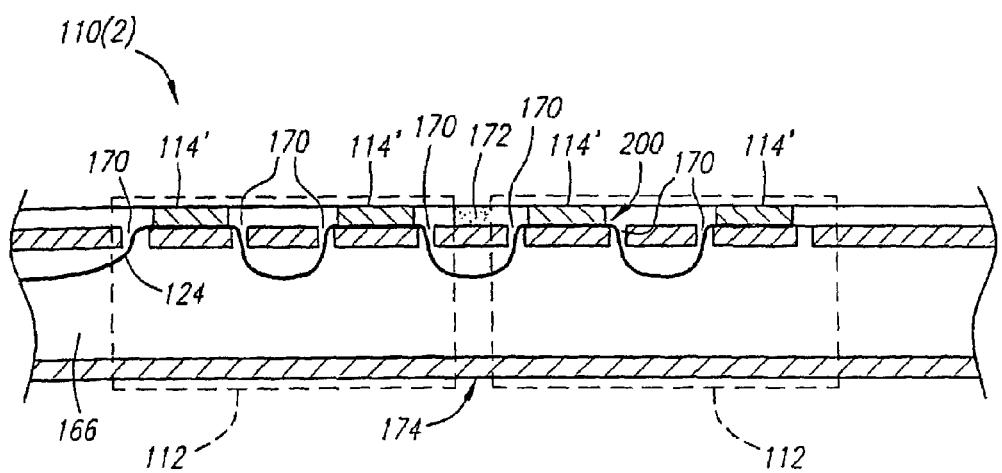
FIG. 11 is a longitudinal sectional view of the probe body of FIG. 10 taken along the line 11—11.

Referring to FIGS. 10 and 11, a probe body 110(2) constructed in accordance with an alternative preferred embodiment of the present inventions is described. The probe body 110(2) is similar to the probe body 110(1) described above, and to the extent that the components of both probe bodies are similar, identical reference numbers have been assigned. The probe body 110(2) differs from the probe body 110(1) in that the data bus 124 does not extend within the entire length of the skive 168 outside of the tube 164, but rather is looped inside the lumen 166 of the tube 164 by interlacing the data bus 124 in and out of pairs of orifices 170 formed through the tube 164 between the sensor chips 114'. In this manner, the probe body 110(1) is configured to bend, while ensuring that the subassembly 200 is not damaged from tensile forces that may otherwise exist absent the loops formed by the data bus 124. To this end, the loops of the data bus 124 are preferably of adequate length to ensure that bending the probe body 110(1) will not result in wire or circuit breakage. A bonding compound (not shown) is preferably disposed within the orifices 170 to provide support for the data bus 124.

Figure 12:
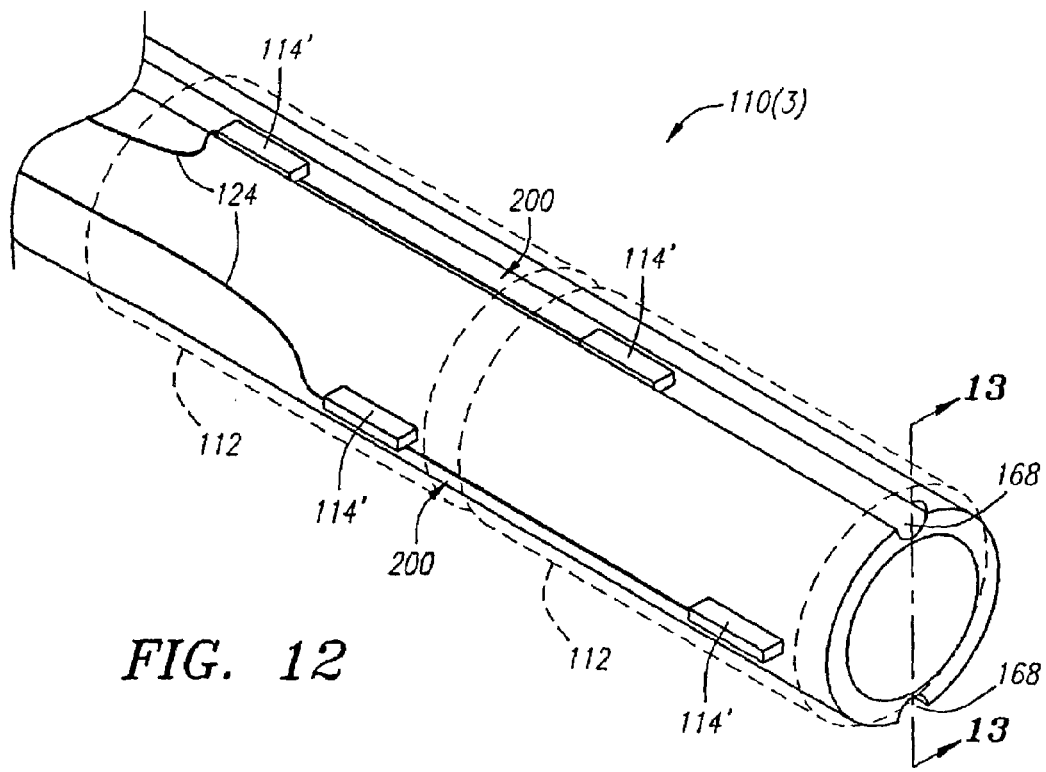
Figure 13:
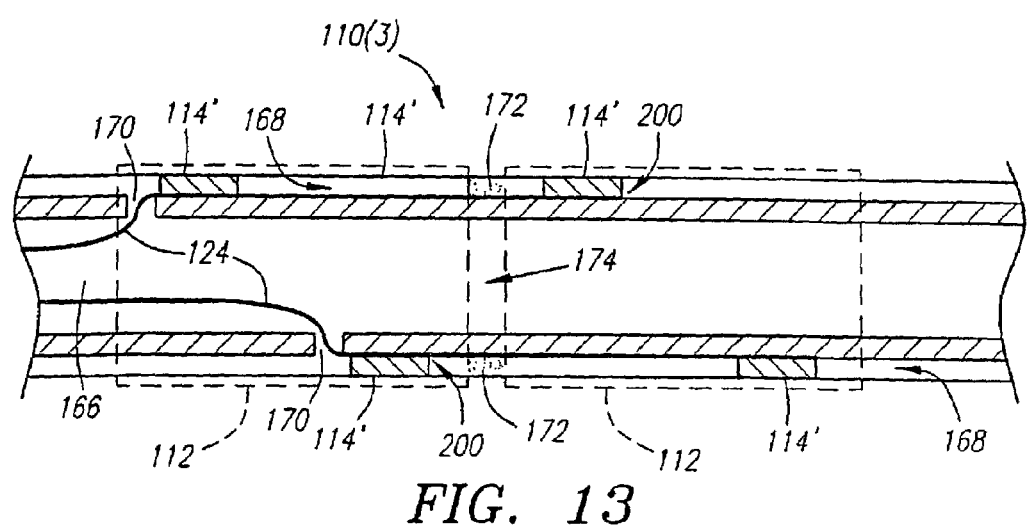
FIG. 13 is a longitudinal sectional view of the probe body of FIG. 12 taken along the line 13—13.

Referring to FIGS. 12 and 13, a probe body 110(3) constructed in accordance with an alternative preferred embodiment of the present inventions is described. The probe body 110(3) is similar to the probe body 110(1) described above, and to the extent that the components of both probe bodies are similar, identical reference numbers have been assigned. The probe body 110(3) differs from the probe body 110(1) in that it comprises two temperature sensor subassemblies 200 that are respectively situated in two skives 168 formed on the opposite sides of the tube 164. In this manner, the probe body 110(3) exhibits temperature sensing capability on both sides of the probe body 110(3), allowing the probe body 110(3) to simultaneously or selectively ablate tissue on opposite sides of the electrodes 112. Of course, more skives 168 can be formed in the tube 164 to accommodate more subassemblies 200. For example, four subassemblies 200 can be respectively situated in four skives 168 formed within the tube 164 to provide temperature sensor capability on four sides of the probe body 110(3).

Figure 14:
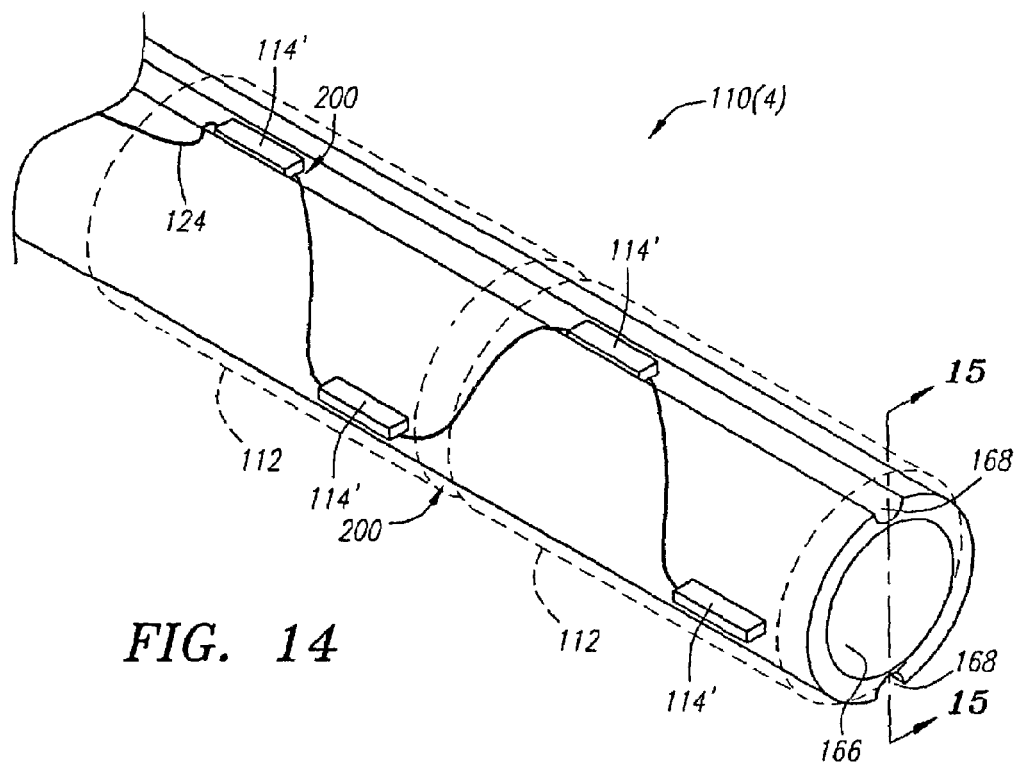
Figure 15:
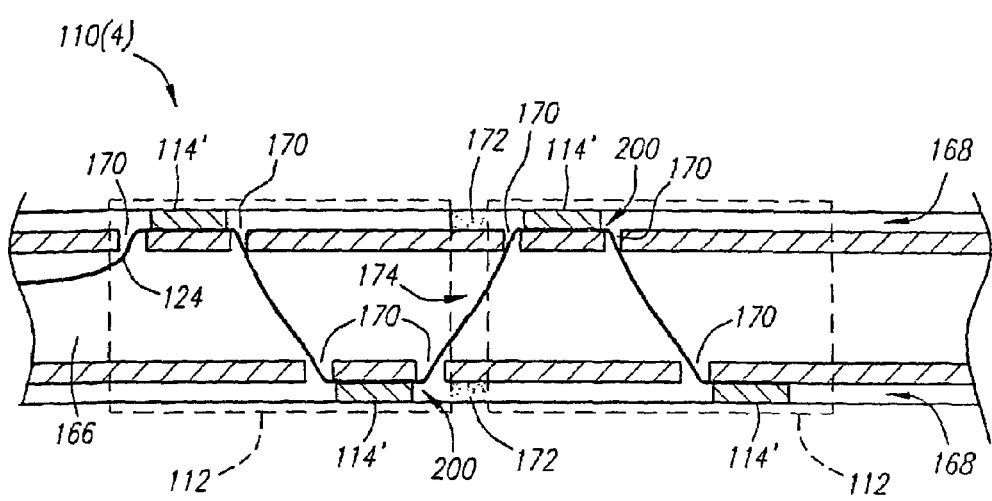
FIG. 15 is a longitudinal sectional view of the probe body of FIG. 14 taken along the line 15—15.

Referring to FIGS. 14 and 15, a probe body 110(4) constructed in accordance with an alternative preferred embodiment of the present inventions is described. The probe body 110(4) is similar to the probe body 110(1) described above, and to the extent that the components of both probes bodies are similar, identical reference numbers have been assigned. The probe body 110(4) differs from the probe body 110(1) in that it comprises a single temperature sensor subassembly 200 that is situated in two skives 168 formed on the opposite sides of the tube 164. Specifically, alternating sensor chips 114' are mounted within the respective skives 168, with the data bus 124 traversing the lumen 166 between the opposite sides of the tube 164. To this end, pairs of orifices 170 are formed through the tube 164 adjacent the opposite edges of each sensor chip 114, allowing the data bus 124 to extend between the skives 168 and the lumen 164. Like the probe body 110(2) described above, a sealing material 172 is suitably disposed within the skives 168 between the electrodes 112 to seal the sensor chips 114' within the skives 168.

Figure 16:
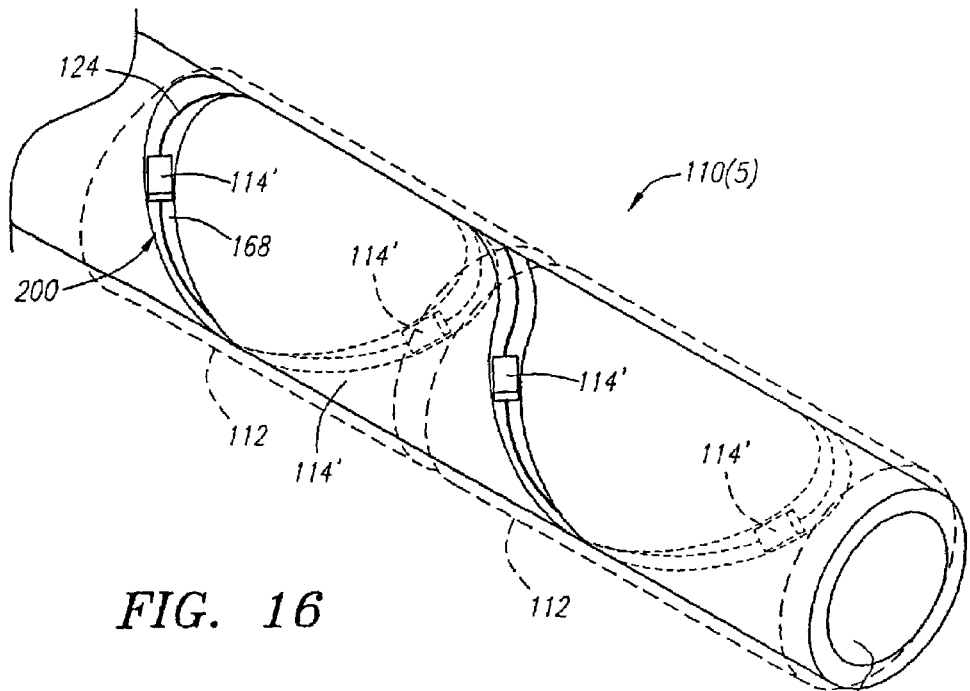

Referring to FIG. 16, a probe body 110(5) constructed in accordance with an alternative preferred embodiment of the present invention is described. The probe body 110(5) is similar to the probe body 110(1) described above, and to the extent that the components of both probe bodies are similar, identical reference numbers have been assigned. The probe body 110(5) differs from the probe body 110(1) in that the skive 168 is formed in the tube 164 in a spiral configuration. In this manner, the single temperature subassembly 200 is situated in the skive 168, and is thus also in a spiral configuration, with the sensor chips 114' being disposed on opposite sides of the tube 164. Although the sensor chips 114' are shown disposed on opposites sides, the spiral configuration of the skive 168 allows circumferential placement of the sensor chips 114' anywhere on the tube 164.

Medical Probes with Temperature Sensor Subassemblies and Tip Electrode

Figure 17:
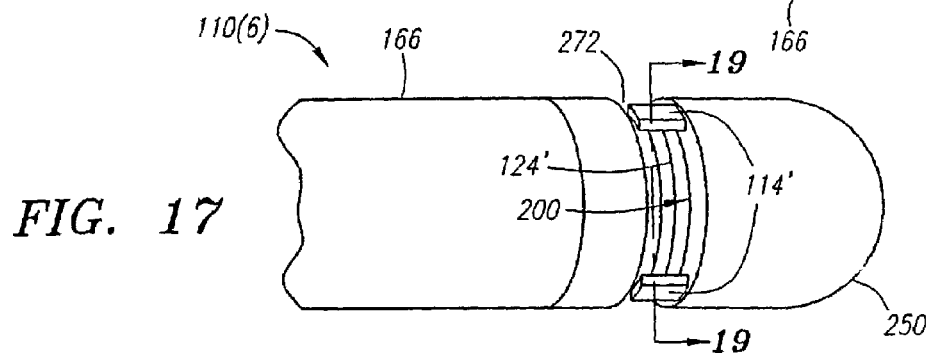
Figure 18:
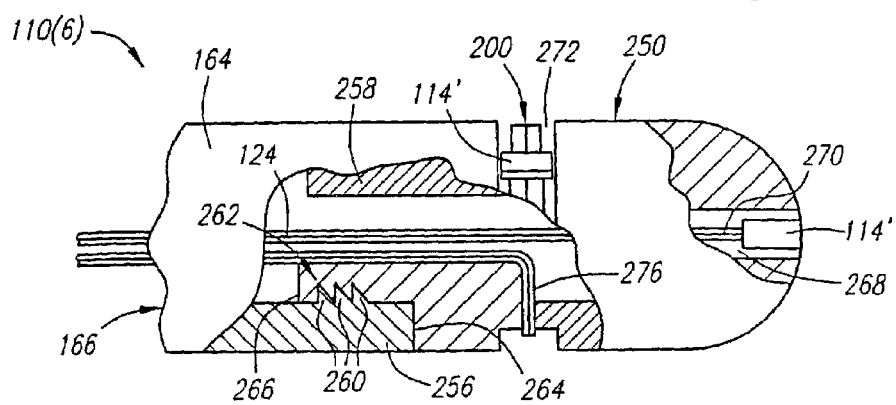
FIG. 18 is a partially cut-away side view of the probe body of FIG. 17.
Figure 19:
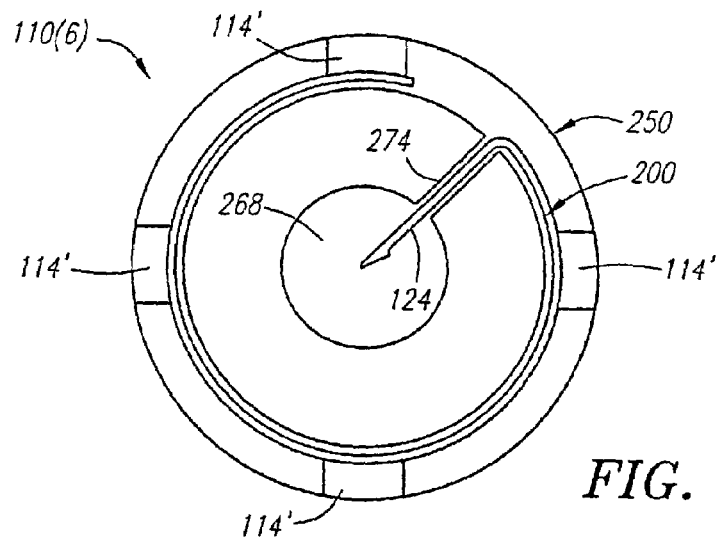
FIG. 19 is a cross-sectional view of an electrode tip assembly employed in the probe body of FIG. 17 taken along the line 19—19.

Referring to FIGS. 17, 18, and 19, a probe body 110(6) constructed in accordance with a preferred embodiment of the present inventions is described. Like the probe bodies described above, the probe body 110(6) comprises an elongate tube 164 through which a lumen 166 extends. Rather than carrying a plurality of segmented electrodes, the tube 164 carries a single tip electrode 250. The tip electrode 250 is preferably composed of an electrically conductive and biocompatible material, such as platinum-iridium, gold, or other metallic material.

The tip electrode 250 is mounted to the distal end of the tube 164. Specifically, the tube 164 has an open distal end 256 in which a proximal mounting portion 258 of the tip electrode 250 is secured. To facilitate attachment of the tip electrode 250 to the tube 164, the inner surface of the open distal end 256 and the outer surface of the proximal mounting portion 258 are provided with a series of corresponding annular ridges 260 and annular indentations 262, respectively, which engage each other when the mounting portion 258 is inserted into the open distal end 256. To ensure an integral fit, the ridges 260 and indentations 262 are slanted in the proximal direction, such that the mounting portion 258 and open distal end 256 are interlocked when engaged. Specifically, the ridges 260 and indentations 262 are preferably shaped in a triangular configuration with an angled distal contact surface 264 and a proximal contact surface 266 oriented perpendicularly relative the longitudinal axis of the probe body 110(6).

The tip electrode 250 includes a lumen 268, which is in axial communication with the lumen 166 of the tube 164, thereby allowing electrical circuitry to be routed from the tip electrode 250 back to the proximal end of the probe body 110(6). The probe body 110(6) includes a temperature sensor capability at the distal tip of the tip electrode 250. To this end, a sensor chip 114' is mounted at the extreme distal end of the cap lumen 268 in contact with the inner surface of the tip electrode 250 distal tip. A data bus 270 extends from the sensor chip 114' back through the lumens 268 and 166, to the proximal end of the probe body 110(6). Like the distal common data bus 124 described above, the data bus 270 may include three electrical paths (data line, ground line, and power line), or two electrical paths (data/power line and ground line).

The probe body 110(6) further includes a temperature sensor capability around the circumference of the tip electrode 250. To this end, a single temperature sensor subassembly 200 is circumferentially disposed about the tip electrode 250. Like the aforementioned probe bodies 110, the probe body 110(6) is configured such that it exhibits a reduced profile. To this end, the subassembly 200 is situated within an annular skive 272 formed around the tip electrode 250. As illustrated, the digital temperature sensor chips 114' are mounted within the skive 272 at the junction of the proximal end of the tip electrode 250 and the distal end of the tube 164. Additionally, a filling material, such as, e.g., an ultraviolet sensitive adhesive or an epoxy, preferably is applied to the annular skive 272 in order to seal the skive 272 and protect the subassembly 200 from the ambient environment. Preferably, the sensor chips 114' are in contact with the tip electrode 250, providing a more accurate temperature reading of the tissue during the ablation process. A bore hole 274 (best shown in FIG. 19) is radially made through the wall of the tip electrode 250 between the skive 272 and lumen 268, allowing the data bus 124 of the subassembly 200 to be routed therethrough.

Figure 20:
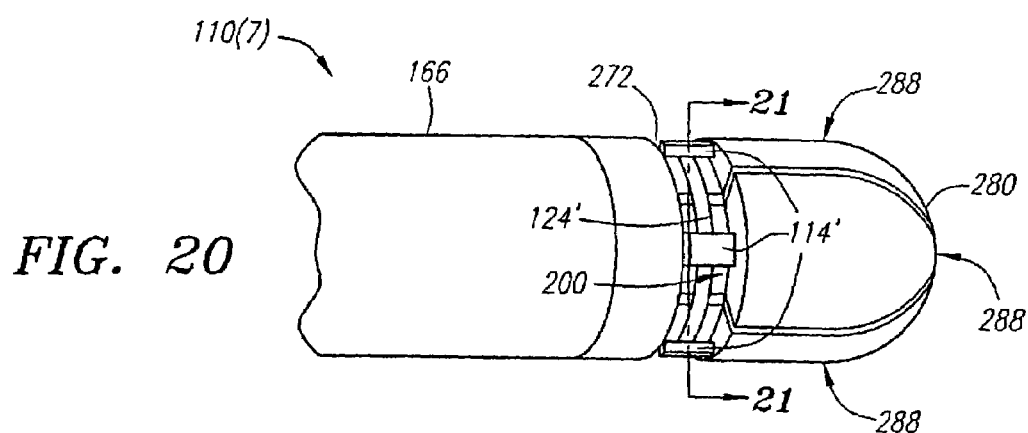
Figure 21:
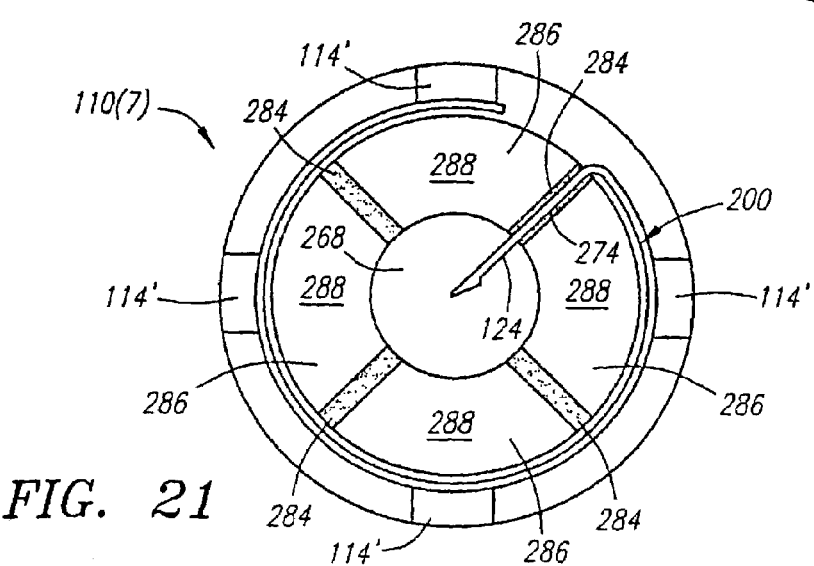
FIG. 21 is a cross-sectional view of an electrode tip assembly employed in the probe body of FIG. 20 taken along the line 21—21.

Referring to FIGS. 20 and 21, a probe body 110(7) constructed in accordance with an alternative preferred embodiment of the present invention is described. The probe body 110(7) is similar to the probe body 110(6) described above, and to the extent that the components of both probe bodies are similar, identical reference numbers have been assigned. The probe body 110(7) differs from the probe body 110(6) in that probe body 110(7) comprises a segmented tip electrode 280 divided into wedge sections. Four wedge sections are illustrated, although the number of wedge sections may be more or less than four sections. Specifically, the tip electrode 280, in this example, is divided into four radial sections 288 that are separated by insulators 284, and four electrodes 286, which are separated by the same insulators 284. Each section 288 is electrically isolated from the adjacent section 288 by one of the insulators 284, and can thus be separately controlled. The temperature sensor arrangement is similar to that described above with respect to the probe body 110(6), with the exception that the bore hole 274 is formed radially through one of the insulators 284 between the skive 272 and the lumen 268.

It should be noted that the above-described medical probes 110(6) and (7) can optionally include segmented electrodes, in which case, further temperature sensor subassemblies 200 can be implemented in a manner described above with respect to the medical probes 110(1)–(5).

It should also be appreciated that other types of tip electrodes may be used with the above-described medical probes 110(6) and (7), such as the tip electrode described in U.S. Pat. No. 6,022,346 to Panescu, et al., filed Feb. 8, 2000, which is expressly and fully incorporated herein by reference.

Custom Electrode

Figure 22:
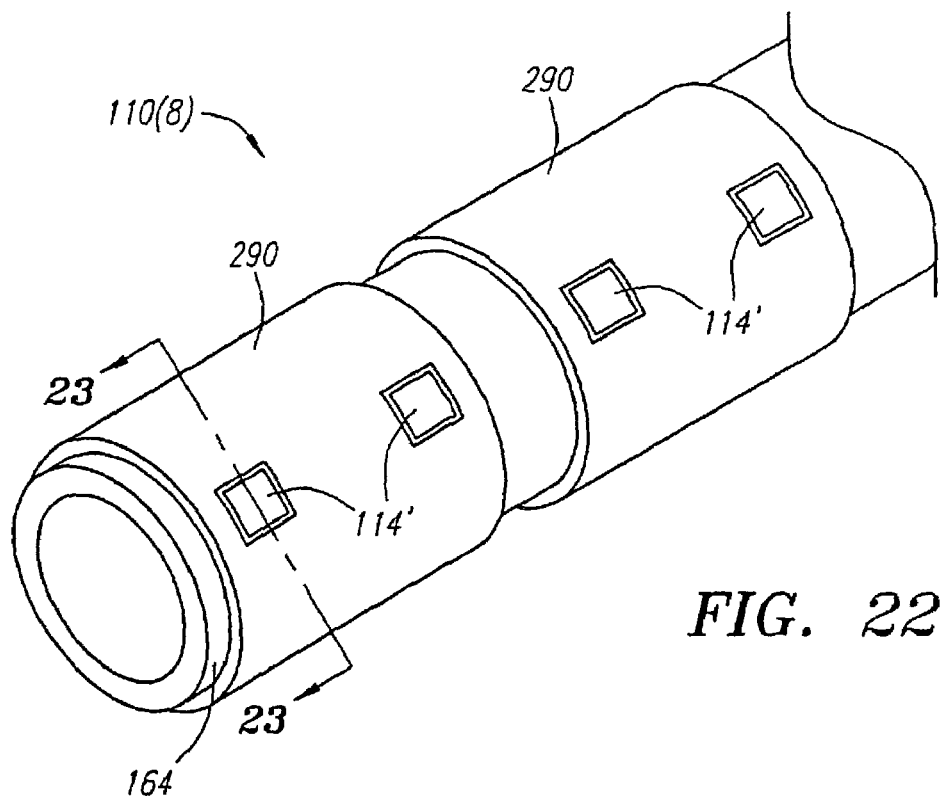
Figure 23:
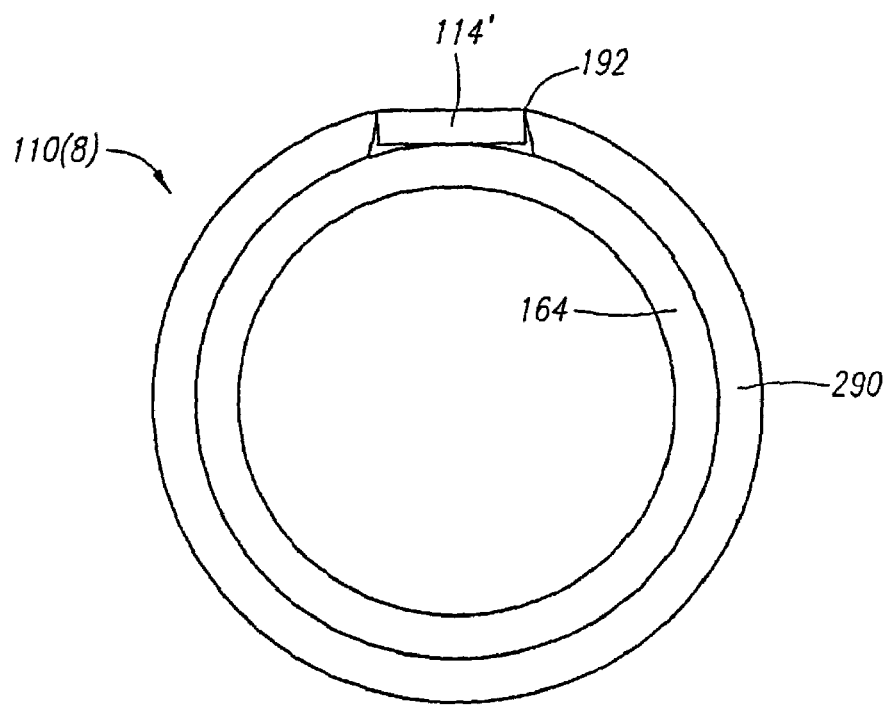
FIG. 23 is a cross-sectional view of the probe body of FIG. 22 taken along the line 23—23.

Referring to FIGS. 22 and 23, a probe body 110(8) constructed in accordance with an alternative preferred embodiment of the present inventions is described. The probe body 110(8) is similar to the probe body 110(1) described above, and to the extent that the components of both probe bodies are similar, identical reference numbers have been assigned. The probe body 110(8) differs from the probe body 110(1) in that it includes customized electrodes 290 that are designed to further reduce the profile of the probe body 110(8). Specifically, beveled openings 192 (shown best in FIG. 21) are formed through the electrodes 290. The sensor chips 114' are firmly mounted within the beveled openings 192. As illustrated in FIG. 23, the beveled opening 192 is cut so that it is larger on the inside surface of the electrode 290 as compared to the outer surface of the electrode 290. A sensor chip 114' is then placed into the beveled opening 192 from the underside of the electrode 290. Thus, the sensor chip 114' is held tightly between the exterior surface of the tube 164 and the tapered surface of the beveled opening 192 when the electrode 290 is mounted on the tube 164.

By using this electrode 192, the sensor chip 114' is placed almost at the tissue surface. As previously discussed, the sensor chip 114' is preferably in contact with a metallic surface of the electrode 290. The design of the electrode 290 allows this to be accomplished without increasing the profile of the probe body 110(8). Additionally, this electrode 290 enables a sensor chip 114' to be placed closer to the tissue being measured and ablated since the electrode 290 does not cover the surface of the sensor chip 114' that detects temperature. The electrode 290 is shown pressure fitted around the tube 164 and is depicted as a segmented electrode. However, other electrodes, including coil electrodes, may be similarly configured with specially designed beveled openings.

Single Sensor System

In the previously discussed preferred embodiments, multiple temperature sensor chips 114' are used to measure the temperature of tissue targeted for ablation. Since the sensor chips 114' communicate digitally, the use of just one single sensor 114' has the potential to offer more immunity to electrical noise in the environment compared to a conventional sensor that outputs low-level analog signals. Consequently, a single digital temperature sensor 114', rather than multiple sensors 114', may be advantageously employed to obtain temperature sensor data during the ablation process. Therefore, the use of one sensor chip 114', rather than multiple sensor chips 114', still provides an advantage over the use of analog temperature sensors, since analog sensors are susceptible to small amounts of electrical noise.

Multiplexed Systems

Another manner in which the number of wires within a medical probe and associated connecting cable can be reduced involves multiplexing the temperature signals output from the temperature sensors. Such multiplexing may be accomplished using, e.g., digitally controlled switches, voltage controlled oscillators, and filters.

Figure 24:
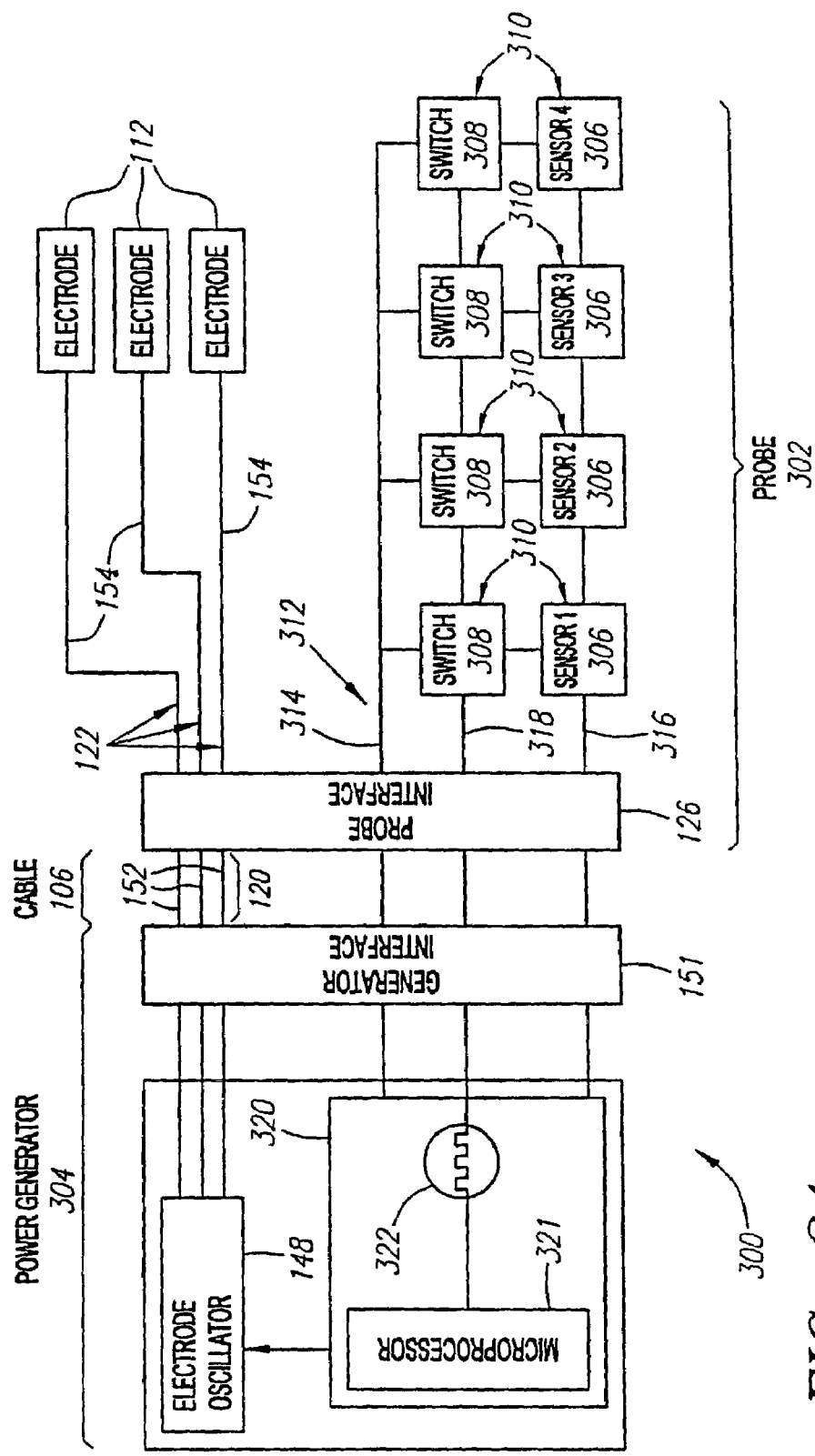
FIG. 24 is a schematic diagram of a preferred embodiment of an electrical circuit implemented in a medical probe system, wherein digital or analog temperature sensors are connected to a power generator through common electrical paths located in the medical probe and connecting cable.

FIG. 24 illustrates a schematic diagram of system 300, which is similar to the system 100 described above with the exception that the system 300 utilizes a multiplexing methodology. To the extent that the components of the systems 100 and 300 are common, identical reference numbers have been assigned. The system 300 includes a probe 302, which is connected to an RF power generator 304 via the cable 106. The probe 302 includes a plurality of analog or digital temperature sensors 306 (sensors 1–4), such as thermistors, thermocouples, resistance temperature detectors (RTD's), or digital temperature sensor chips, that are multiplexed using digitally controlled switches 308. Specifically, the switches 308 are respectively connected to the temperature sensors 306, which in combination, form switched sensor subassemblies 310. The switch 308 and temperature sensor 306 within each assembly can be discrete with respect to each other, or alternatively, can be combined into switch/sensor modules or hybrid circuits. A common data bus 312, which comprises a data line 314, ground line 316, and control line 318, is coupled distally to the switched sensor subassemblies 310.

Specifically, the switched sensor subassemblies 310 are coupled in parallel to the common data bus 312, with the data line 314 being coupled to the switch side of the switched sensor subassemblies 310, the ground line 316 being coupled to the sensor side of the switched sensor subassemblies 306, and the control line 318 being coupled to the switches 308. The switches 308 are encoded such that a clock signal applied thereto closes the switches 308 one at a time in a sequential and predetermined order, thereby providing a means to obtain temperature sensor data from each sensor 306 using the single data line 314. To this end, the common data bus 312 is proximally coupled to temperature control circuitry 320 within the RF power generator 304. The temperature control circuitry 320 comprises a microprocessor 321 that is configured for generating and transmitting a clock signal 322 to the sensor assemblies 310 over the control line 318. As the clock signal 322 triggers each switch 308 to close, the respective sensor 306 is connected between the data and ground lines 310 and 312, thereby allowing the microprocessor 321 to read the temperature data output from the respective sensor 306.

Figure 25:
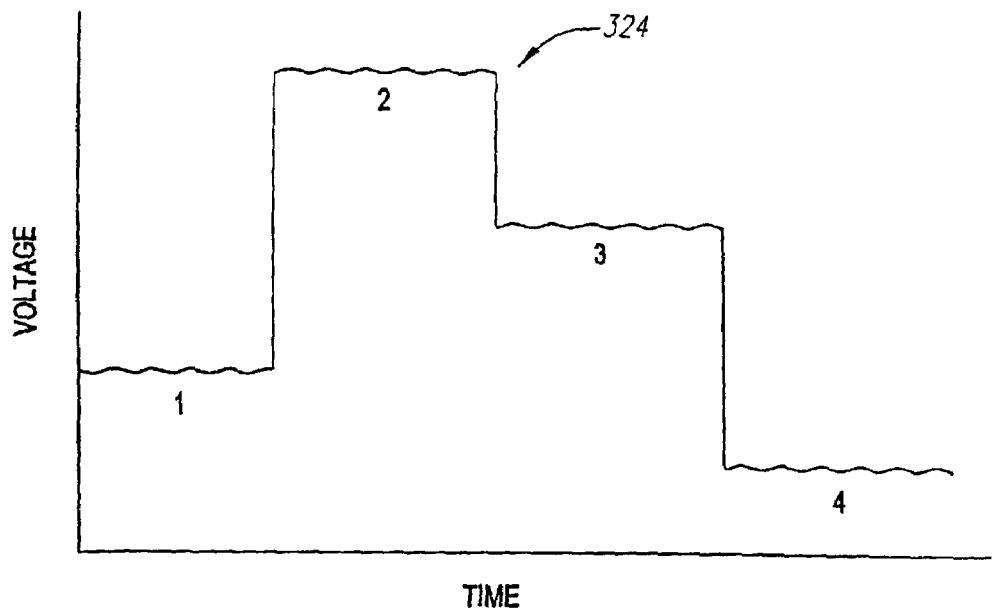
FIG. 25 is an exemplary waveform of temperature data output from the analog version of the electrical circuit of FIG. 24.

FIG. 25 illustrates an exemplary temperature signal 324 for the analog version of the system 300 from which temperature data can be obtained for each sensor 306. This temperature data is represented by four different discrete voltage levels appearing in the temperature signal 324 over four respective time periods 1–4. Thus, temperature data for any of the sensors 1–4 can be obtained based on the voltage value of the temperature signal 324 at the corresponding time period. The advantages of operating all sensors 306 on the same three wires would be similar to those found in the above-described embodiments. That is, the number of electrical paths necessary to implement the system is reduced as compared to a conventional system.

Figure 26:
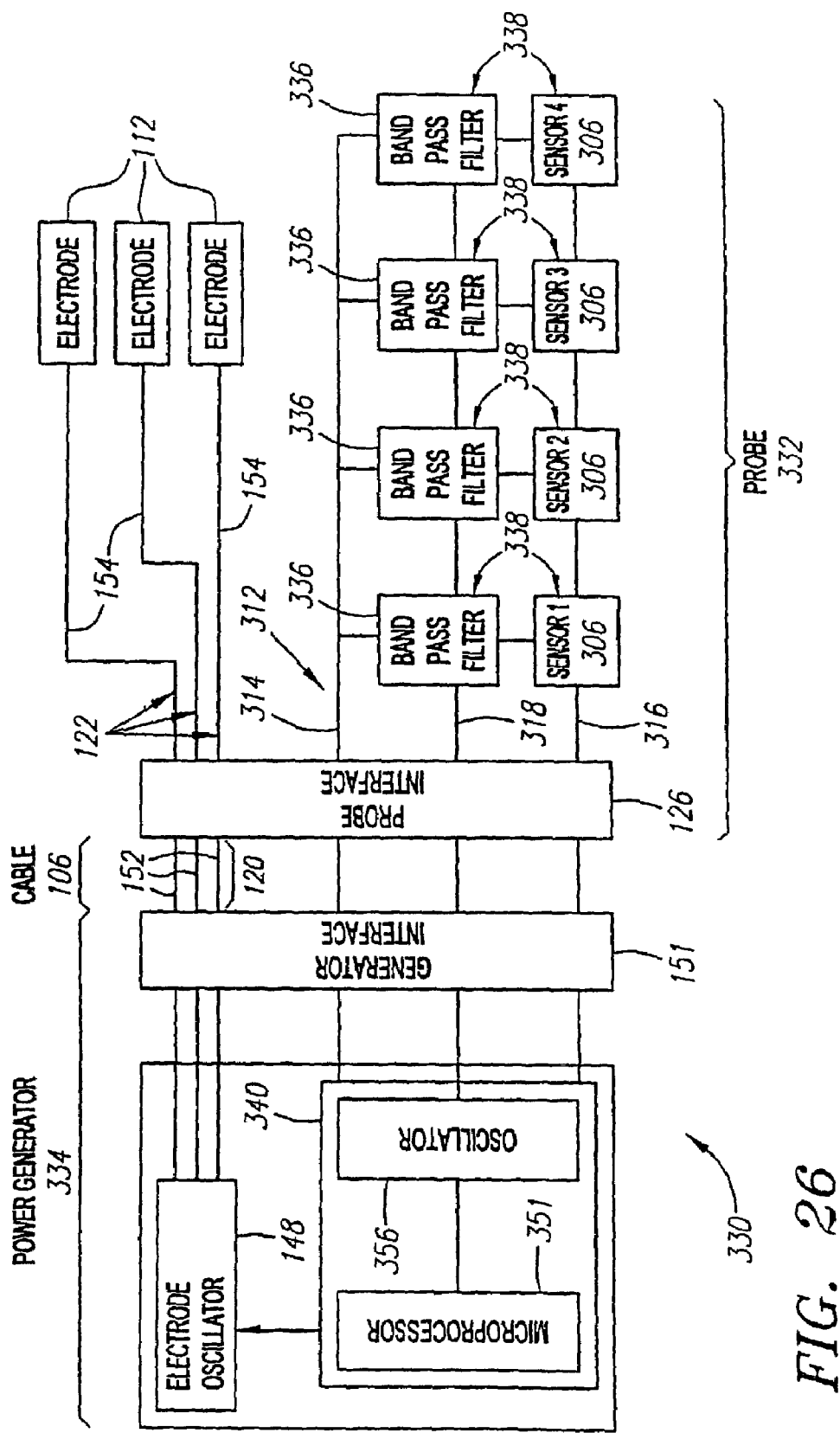
FIG. 26 is a schematic diagram of an alternative preferred embodiment of an electrical circuit implemented in a medical probe system, wherein temperature sensors are connected to a power generator through common electrical paths located in the medical probe and connecting cable.

FIG. 26 illustrates a schematic diagram of a system 330 that includes a probe 332 and an RF power generator 334. The system 330 is similar to the above-described system 300, with the exception that it utilizes band-pass filters 336, rather than the digital switches 308, to obtain temperature data from the sensors 306 one at a time. Specifically, the band-pass filters 336 are respectively connected to the temperature sensors 306, which in combination, form filtered sensor subassemblies 338. The filter 336 and temperature sensor 306 within each assembly can be discrete with respect to each other, or alternatively, can be combined into filtered sensor modules or hybrid circuits. The filtered sensor subassemblies 338 are coupled in parallel to the common data bus 312, with the data line 314 being coupled to the filter side of the filtered sensor subassemblies 338, the ground line 316 being coupled to the sensor side of the filtered sensor subassemblies 338, and the control line 318 being coupled to the filters 336.

Each band-pass filter 336 is tuned to a distinct frequency, such that a plurality of frequencies applied thereto allows signals to pass one at a time in a sequential and predetermined ordered, thereby providing a means to obtain temperature sensor data from each sensor 306 using the single data line 314. To this end, the common data bus 312 is proximally coupled to temperature control circuitry 340 within the RF power generator 334. The temperature control circuitry 340 includes an oscillator 356, which is configured for generating and transmitting a frequency sweep to the sensor assemblies 338 over the control line 318. The frequency sweep encompasses all of the distinct frequencies to which the band-pass filters 336 are tuned. Thus, during one frequency sweep, the sensors 306 are connected between the data and ground lines 310 and 312 one at a time, thereby allowing a microprocessor 351 of the temperature control circuitry 340 to read the temperature data output from the respective sensor 306.

Figure 27:
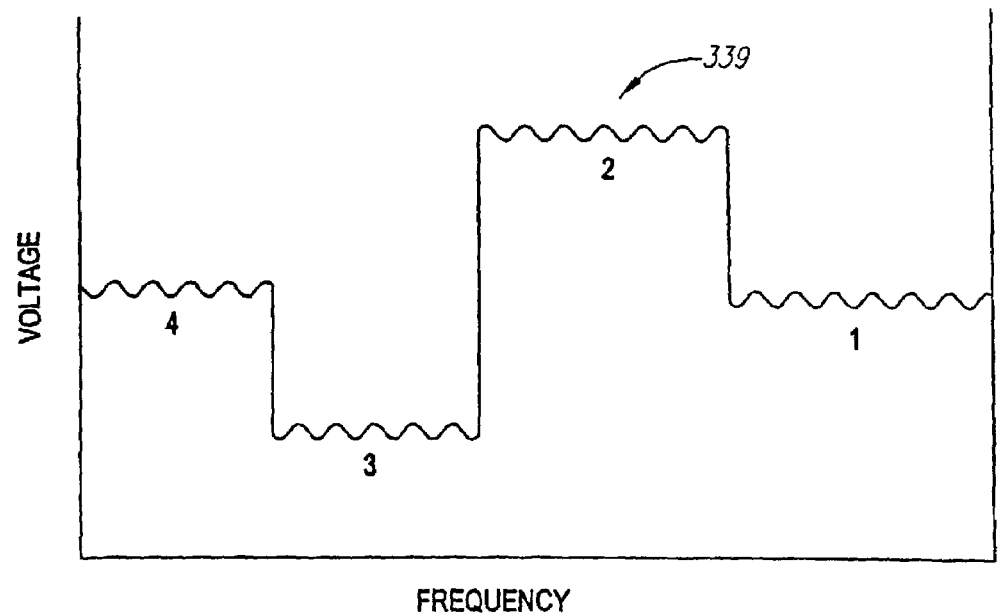
FIG. 27 is an exemplary waveform of temperature data output from the electrical circuit of FIG. 26.

FIG. 27 illustrates an exemplary temperature signal 344 from which temperature data can be obtained for each sensor 306. This temperature data is represented by four different discrete voltage levels appearing in the temperature signal 339 over four respective frequency ranges 1–4. Thus, temperature data for any of the sensors 1–4 can be obtained based on the voltage value of the temperature signal 339 at the corresponding frequency range. Again, the advantages of operating all sensors 306 on the same three wires would be similar to those found in the above-described embodiments. That is, the number of electrical paths necessary to implement the system is reduced as compared to a conventional system.

Figure 28:
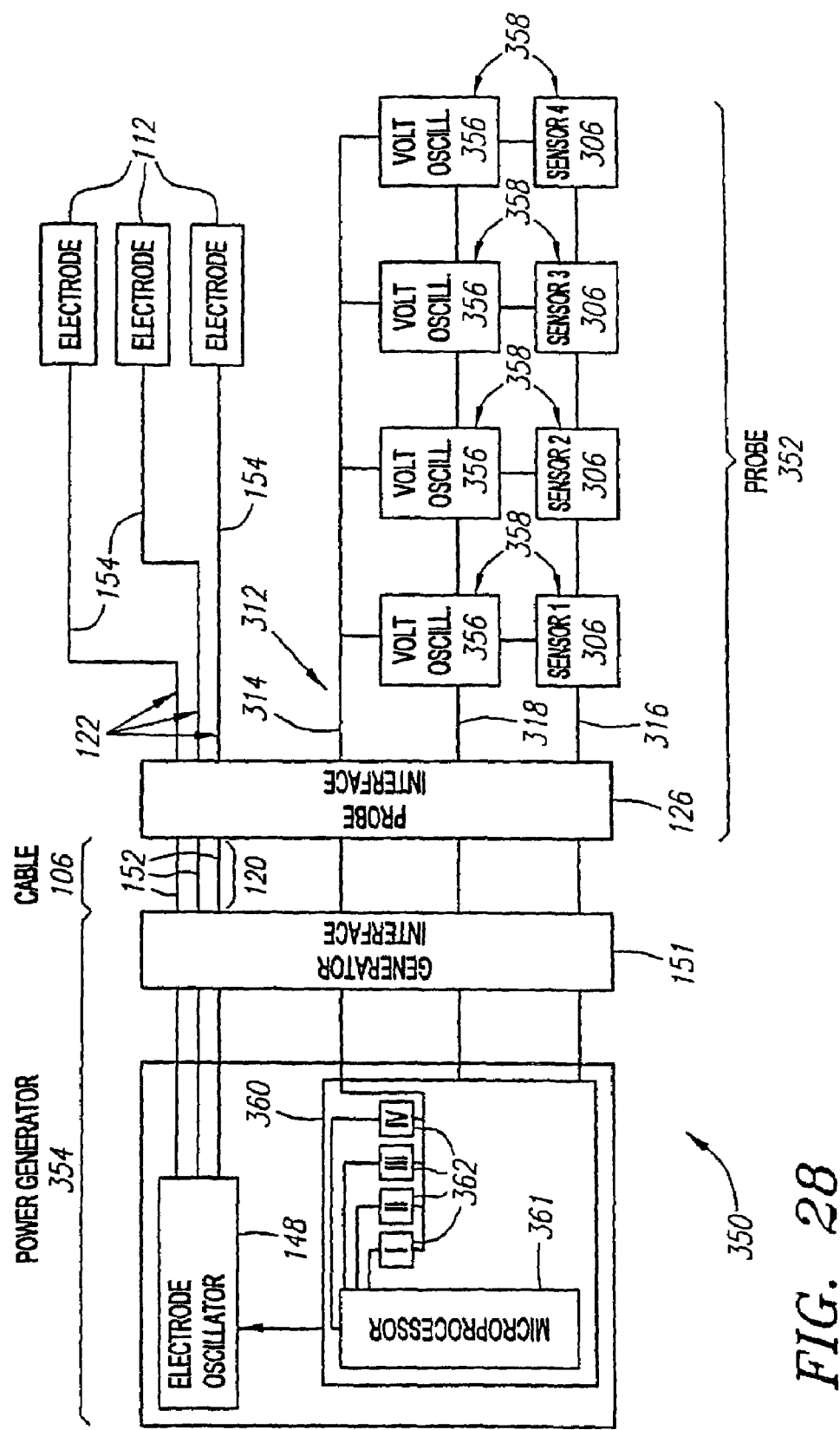
FIG. 28 is a schematic diagram of an alternative preferred embodiment of an electrical circuit implemented in a medical probe system, wherein temperature sensors are connected to a power generator through common electrical paths located in the medical probe and connecting cable.
Figure 29:
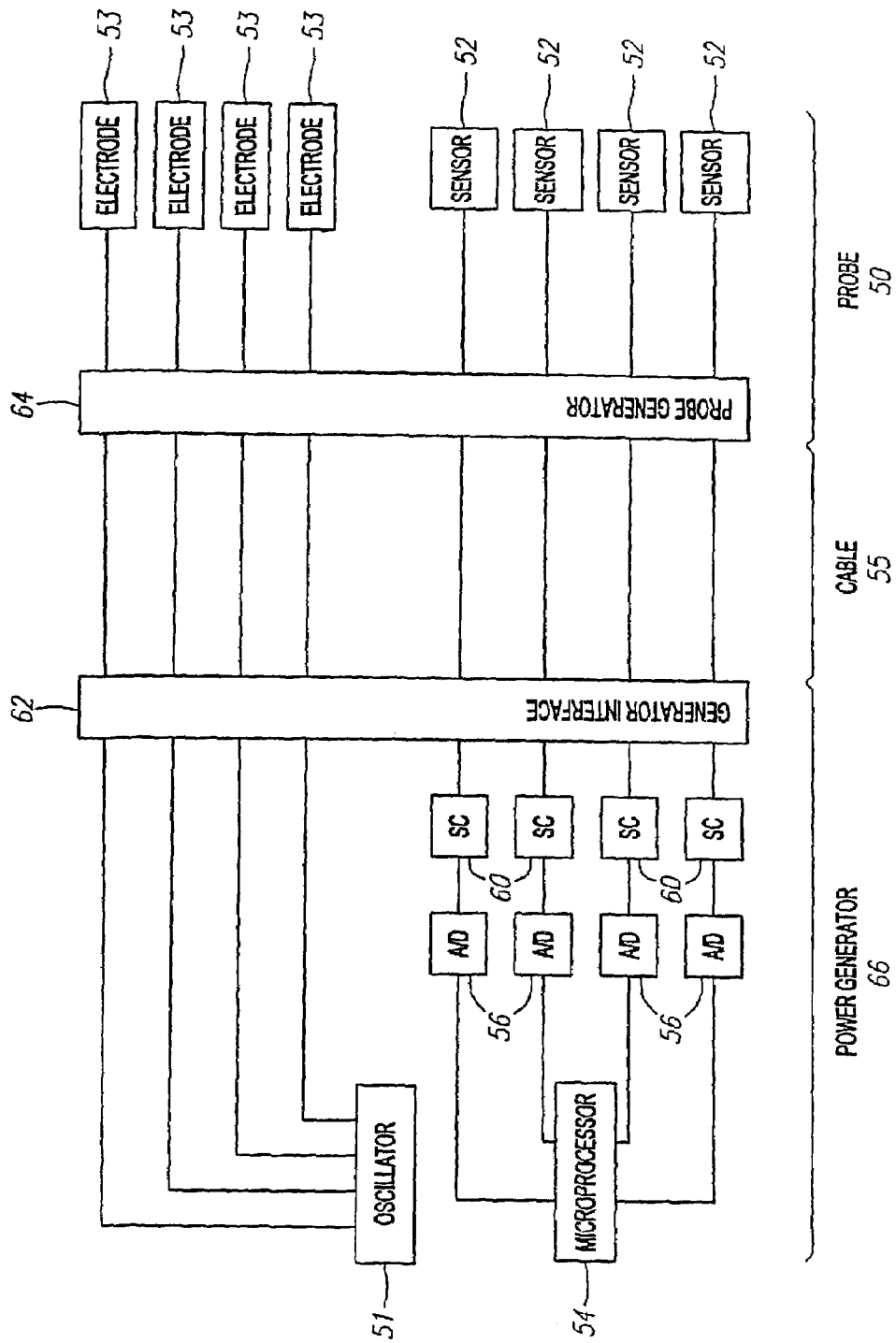
FIG. 29 is a schematic diagram of prior art power generator and medical probe system.
Figure 30:
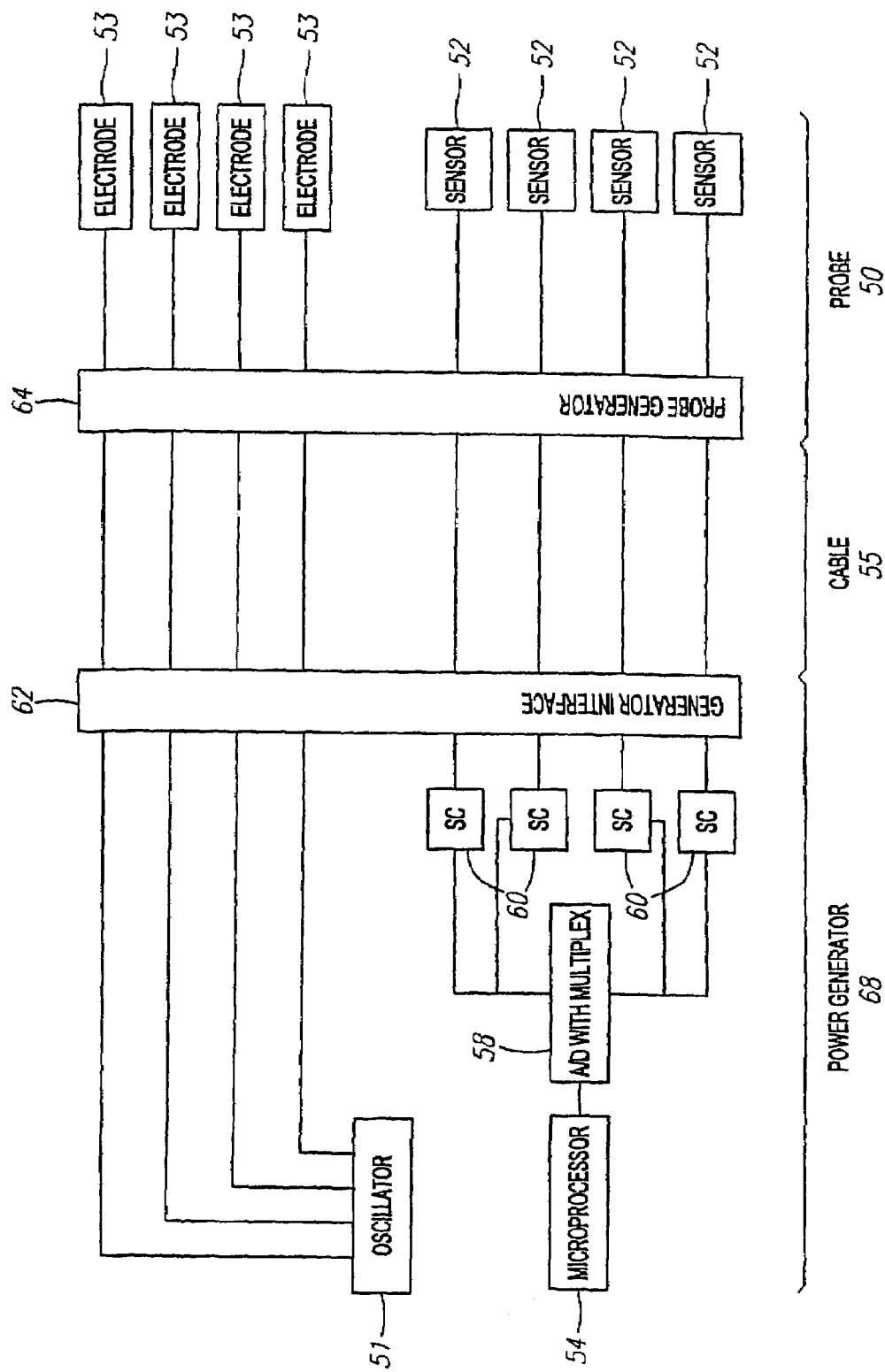
FIG. 30 is a schematic diagram of another prior art power generator and medical probe system.

FIG. 28 illustrates a schematic diagram of a system 350 that includes a probe 352 and an RF power generator 354. The system 350 is similar to the above-described system 300, with the exception it utilizes voltage controlled oscillators 356, rather than the digital switches 308, to obtain temperature data from the sensors 306 one at a time. Specifically, the oscillators 356 are respectively connected to the temperature sensors 306 to form oscillating sensor subassemblies 358. The oscillator 356 and temperature sensor 306 within each assembly can be discrete with respect to each other, or alternatively, can be combined into filtered sensor modules or hybrid circuits. The oscillating sensor subassemblies 358 are coupled in parallel to the common data bus 312, with the data line 314 being coupled to the oscillator side of the oscillating sensor subassemblies 358, the ground line 316 being coupled to the sensor side of the oscillating sensor subassemblies 358, and the control line 318 being coupled to the oscillators 356.

Each oscillator 356 resonates at a distinct frequency proportional to the voltage output from the respective sensor 306 connected to the oscillator 356. Thus, the signal output from each oscillating sensor subassembly 358 will contain temperature data in the form of a frequency modulated signal. To this end, the common data bus 312 is proximally coupled to temperature control circuitry 360 within the RF power generator 354. The temperature control circuitry 360, via the control line 318, routes voltage power to each oscillating sensor subassembly 358 in order to control the voltage controlled oscillators 356. The temperature control circuitry 360 further includes band-pass filters 362$i$, 362$ii$, 362$iii$, and 362$iv$, each of which is tuned to a selected one of the center frequencies at which the oscillators 356 resonate. The band-pass filters 362 filter the signals transmitted by the oscillators 356 via the data line 314, which are then read by a microprocessor 361. Thus, the four frequency modulated signals are transmitted on the common data bus 312 simultaneously, which signals are then decoded by the band-pass filters 362$i$, 362$ii$, 362$iii$, and 362$iv$. Although the band-pass filters 362 are housed in the RF generator 354 in the illustrated embodiment, they may alternatively be housed within the probe handle of the medical probe (not shown). Again, the advantages of operating all sensors 306 on the same three wires would be similar to those found in the above-described embodiments. That is, the number of electrical paths necessary to implement the system is reduced as compared to a conventional system.

It should be noted that although the temperature sensors 306 are distinguished from each other in the above-described systems 300, 330, and 350 by using different time periods or different frequencies, the temperatures sensors 306 can be distinguished from each other using any orthogonal set of signals. It should also be noted that the switches, filters, or oscillators implemented in the above-described systems 300, 330, and 350 are shown designed into the distal end of a probe, thereby resulting in the reduction of electrical paths within the probe itself, as well as the cable leading back to the ablation power generator. Alternatively, the switches, filters, or oscillators of these systems can be designed into the probe handle, resulting in the reduction of electrical paths only in the cable leading from the handle to the power generator. Placement of this circuitry in the probe handle would be easier to implement due to the relatively small amount of space available in the probe body. This arrangement, however, sacrifices the advantages of electrical path reduction through the probe.

While the invention is susceptible to various modifications and alternative forms, specific examples thereof have been shown by way of example in the drawings and are herein described in detail. The foregoing description of the invention has been presented for purposes of illustration and description. It is not intended to be exhaustive or to limit the invention to the precise forms disclosed. To the contrary, the invention is to cover all modifications, equivalents, and alternatives falling within the spirit and scope of the appended claims.

What is claimed is:

1. A medical probe, comprising:
   an elongate member configured to be used inside of a human body, the elongate member having a proximal end and a distal end;
   a plurality of temperature sensors carried by the distal end of the elongate member; and
   a common electrical bus carried by the elongate member, and defining two or more electrical paths, each of which is coupled to the plurality of temperature sensors.

2. The medical probe of claim 1, wherein the common electrical bus extends through the elongate member and is directly connected to the plurality of temperature sensors.

3. The medical probe of claim 1, further comprising another bus extending through the elongate member, wherein the common electrical bus is located in the proximal end of the elongate member and is indirectly connected to the plurality of temperature sensors through the other bus.

4. The medical probe of claim 1, further comprising an electrode carried by the distal end of the elongate member, wherein one or more of the plurality of temperature sensors is located adjacent the electrode.

5. The medical probe of claim 1, further comprising a plurality of electrodes carried by the distal end of the elongate member, wherein the plurality of temperature sensors are respectively located adjacent the plurality of electrodes.

6. The medical probe of claim 1, further comprising a handle mounted to the proximal end of the elongate member, wherein the handle comprises an interface to connect a cable to the two or more electrical paths, the cable providing a connection between the probe and an ablation power generator.

7. The medical probe of claim 1, wherein the two or more electrical paths comprise a data line and a ground line.

8. The medical probe of claim 1, wherein the two or more electrical paths comprise a data line, a ground line, and a power line.

9. The medical probe of claim 1, wherein each of the two or more electrical paths comprises a single wire.

10. The medical probe of claim 1, wherein the temperature sensors are connected in parallel to the two or more electrical paths.

11. A medical probe, comprising:
    an elongate member configured to be used inside of a human body, the elongate member having a proximal end and a distal end;
    a plurality of temperature sensors carried by the distal end of the elongate member; and
    a common electrical bus extending between the proximal and distal ends of the elongate member, and defining two or more electrical paths, each of which is coupled to the plurality of temperature sensors.

12. The medical probe of claim 11, wherein the common electrical bus is directly connected to the plurality of temperature sensors.

13. The medical probe of claim 11, further comprising an electrode carried by the distal end of the elongate member, wherein one or more of the plurality of temperature sensors is located adjacent the electrode.

14. The medical probe of claim 11, further comprising a plurality of electrodes carried by the distal end of the elongate member, wherein the plurality of temperature sensors are respectively located adjacent the plurality of electrodes.

15. The medical probe of claim 11, further comprising a handle mounted to the proximal end of the elongate member, wherein the handle comprises an interface to connect a cable to the two or more electrical paths, the cable providing a connection between the probe and an ablation power generator.

16. The medical probe of claim 11, wherein the two or more electrical paths comprise a data line and a ground line.

17. The medical probe of claim 11, wherein the two or more electrical paths comprise a data line, a ground line, and a power line.

18. The medical probe of claim 11, wherein each of the two or more electrical paths comprises a single wire.

19. The medical probe of claim 11, wherein the temperature sensors are connected in parallel to the two or more electrical paths.

* * * * *